(12) United States Patent
Honore et al.

(10) Patent No.: US 12,336,798 B2
(45) Date of Patent: Jun. 24, 2025

(54) WEARABLE DEVICE WITH MULTIMODAL DIAGNOSTICS

(71) Applicant: Alio, Inc., San Francisco, CA (US)

(72) Inventors: Francis Honore, San Francisco, CA (US); Samit Kumar Gupta, Bel Air, MD (US); David John Kuraguntla, Bel Air, MD (US); James Reich, San Francisco, CA (US); Anthony Flannery, Jr., Bainbridge Island, WA (US); Jivko Mihaylov, San Jose, CA (US)

(73) Assignee: Alio, In., Broomfield, CO (US)

( * ) Notice: Subject to any disclaimer, the term of this patent is extended or adjusted under 35 U.S.C. 154(b) by 0 days.

(21) Appl. No.: 17/842,596

(22) Filed: Jun. 16, 2022

(65) Prior Publication Data
US 2022/0304586 A1 Sep. 29, 2022

Related U.S. Application Data

(63) Continuation of application No. 15/702,390, filed on Sep. 12, 2017, now Pat. No. 11,406,274.
(Continued)

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0015* (2013.01); *A61B 5/0022* (2013.01);
(Continued)

(58) Field of Classification Search
CPC . A61B 5/02438; A61B 5/0015; A61B 5/0022; A61B 5/02007; A61B 5/02055;
(Continued)

(56) References Cited

U.S. PATENT DOCUMENTS

| 4,307,618 A | 12/1981 | James et al. |
| 4,575,371 A | 3/1986 | Nordqvist et al. |

(Continued)

FOREIGN PATENT DOCUMENTS

| JP | 4011631 B2 | 11/2007 |
| JP | 2009542421 A | 12/2009 |

(Continued)

OTHER PUBLICATIONS

Dario, et al. Monitoring of prosthetic vascular grafts using piezo-electric polymer sensors. Trans Am Soc Artif Intern Organs. 1983;29:318-22.
(Continued)

*Primary Examiner* — Navin Natnithithadha
(74) *Attorney, Agent, or Firm* — Jonathan D Feuchtwang

(57) ABSTRACT

A system, device and method for automatically and remotely acquiring sensor data from a wearable patch mounted on a patient. An example device implemented as a wearable patch includes a sensor assembly comprising a plurality of sensors configured to detect a corresponding plurality of sensory modalities and generate electrical signals representing the sensory modalities. A signal converter receives the electrical signals from the plurality of sensors and converts the signals to sensor data signals comprising a data representation of at least one of the electrical signals. A communications interface communicates the sensor data signals to a sensor data processing system.

33 Claims, 7 Drawing Sheets

Related U.S. Application Data

(60) Provisional application No. 62/393,590, filed on Sep. 12, 2016.

(51) Int. Cl.

| | |
|---|---|
| *A61B 5/02* | (2006.01) |
| *A61B 5/0205* | (2006.01) |
| *A61B 5/021* | (2006.01) |
| *A61B 5/0245* | (2006.01) |
| *G16H 40/67* | (2018.01) |

(52) U.S. Cl.
CPC ...... *A61B 5/02007* (2013.01); *A61B 5/02055* (2013.01); *A61B 5/02427* (2013.01); *A61B 5/0245* (2013.01); *A61B 5/6824* (2013.01); *A61B 5/6833* (2013.01); *G16H 40/67* (2018.01); *A61B 5/02116* (2013.01); *A61B 5/02444* (2013.01); *A61B 2560/0209* (2013.01); *A61B 2560/029* (2013.01); *A61B 2560/0462* (2013.01); *A61B 2562/0204* (2013.01); *A61B 2562/0219* (2013.01); *A61B 2562/0223* (2013.01); *A61B 2562/0271* (2013.01); *A61B 2562/029* (2013.01)

(58) Field of Classification Search
CPC . A61B 5/02427; A61B 5/0245; A61B 5/6824; A61B 5/6833; A61B 5/02116; A61B 5/02444; A61B 2560/0209; A61B 2560/029; A61B 2560/0462; A61B 2562/0204; A61B 2562/0219; A61B 2562/0223; A61B 2562/0271; A61B 2562/029; G16H 40/67
See application file for complete search history.

(56) References Cited

U.S. PATENT DOCUMENTS

| | | | |
|---|---|---|---|
| 4,600,855 A | 7/1986 | Strachan | |
| 4,920,794 A | 5/1990 | Ingman | |
| 5,241,964 A | 9/1993 | McQuilkin | |
| 5,409,009 A | 4/1995 | Olson | |
| 5,411,551 A | 5/1995 | Winston et al. | |
| 5,522,391 A | 6/1996 | Beaudin et al. | |
| 5,522,394 A | 6/1996 | Zurbruegg | |
| 5,598,841 A | 2/1997 | Taniji et al. | |
| 5,598,847 A | 2/1997 | Renger | |
| 5,681,274 A | 10/1997 | Perkins et al. | |
| 5,760,530 A | 6/1998 | Kolesar | |
| 5,785,657 A | 7/1998 | Breyer et al. | |
| 5,807,258 A | 9/1998 | Cimochowski et al. | |
| 5,967,986 A | 10/1999 | Cimochowski et al. | |
| 5,991,654 A | 11/1999 | Tumey et al. | |
| 5,995,860 A | 11/1999 | Sun et al. | |
| 6,004,348 A | 12/1999 | Banas et al. | |
| 6,015,387 A | 1/2000 | Schwartz et al. | |
| 6,049,727 A | 4/2000 | Crothall | |
| 6,053,873 A | 4/2000 | Govari et al. | |
| 6,173,197 B1 | 1/2001 | Boggett et al. | |
| 6,193,669 B1 | 2/2001 | Degany et al. | |
| 6,206,835 B1 | 3/2001 | Spillman, Jr. et al. | |
| 6,354,999 B1 | 3/2002 | Dgany et al. | |
| 6,416,474 B1 | 7/2002 | Penner et al. | |
| 6,458,086 B1 | 10/2002 | Franco et al. | |
| 6,486,588 B2 | 11/2002 | Doron et al. | |
| 6,682,480 B1 | 1/2004 | Habib et al. | |
| 6,764,519 B2 | 7/2004 | Whitmore | |
| 6,840,956 B1 | 1/2005 | Wolinsky et al. | |
| 7,025,778 B2 | 4/2006 | Hayashi et al. | |
| 7,060,038 B2 | 6/2006 | Letort et al. | |
| 7,261,733 B1 | 8/2007 | Brown et al. | |
| 7,267,651 B2 | 9/2007 | Nelson | |
| 7,307,530 B2 | 12/2007 | Fabian et al. | |
| 7,399,313 B2 | 7/2008 | Brown et al. | |
| 7,452,334 B2 | 11/2008 | Gianchandani et al. | |
| 7,488,345 B2 | 2/2009 | Brown et al. | |
| 7,572,228 B2 | 8/2009 | Wolinsky et al. | |
| 7,650,185 B2 | 1/2010 | Maile et al. | |
| 7,686,842 B2 | 3/2010 | Pavcnik et al. | |
| 7,747,302 B2 | 6/2010 | Milledge et al. | |
| 7,747,329 B2 | 6/2010 | Litvak et al. | |
| 7,785,912 B2 | 8/2010 | Zhan et al. | |
| 7,813,808 B1 | 10/2010 | Doron et al. | |
| 7,918,800 B1 | 4/2011 | Brown et al. | |
| 7,922,667 B2 | 4/2011 | Gianchandani et al. | |
| 7,948,148 B2 | 5/2011 | Porat et al. | |
| 7,949,394 B2 | 5/2011 | Salo et al. | |
| 7,963,920 B2 | 6/2011 | Vilkomerson et al. | |
| 8,016,875 B2 | 9/2011 | Philipp et al. | |
| 8,034,096 B2 | 10/2011 | Hunt | |
| 8,054,140 B2 | 11/2011 | Fleming et al. | |
| 8,114,350 B1 | 2/2012 | Silver et al. | |
| 8,202,311 B2 | 6/2012 | Demetriades et al. | |
| 8,211,165 B1 | 7/2012 | McIntosh et al. | |
| 8,211,166 B2 | 7/2012 | Chuter et al. | |
| 8,211,168 B2 | 7/2012 | Purdy et al. | |
| 8,216,434 B2 | 7/2012 | Hsiai et al. | |
| 8,308,794 B2 | 11/2012 | Martinson et al. | |
| 8,517,941 B1 | 8/2013 | Wenzel | |
| 8,551,156 B2 | 10/2013 | Wack et al. | |
| 8,579,958 B2 | 11/2013 | Kusleika | |
| 8,597,343 B2 | 12/2013 | Bliss et al. | |
| 8,628,491 B2 | 1/2014 | Kahn et al. | |
| 9,427,305 B2 | 8/2016 | Kuraguntla et al. | |
| 9,662,021 B2 | 5/2017 | Chow et al. | |
| 9,924,905 B2 | 3/2018 | Kuraguntla et al. | |
| 10,542,931 B2 | 1/2020 | Kuraguntla et al. | |
| 11,045,123 B2 * | 6/2021 | Honore | A61B 5/1455 |
| 11,406,274 B2 | 8/2022 | Honore et al. | |
| 2001/0041932 A1 | 11/2001 | Scholz et al. | |
| 2001/0049554 A1 | 12/2001 | Ruiz et al. | |
| 2002/0183628 A1 | 12/2002 | Reich et al. | |
| 2003/0053284 A1 | 3/2003 | Stevenson et al. | |
| 2004/0082867 A1 | 4/2004 | Esch et al. | |
| 2004/0082868 A1 | 4/2004 | Campbell et al. | |
| 2004/0133089 A1 | 7/2004 | Kilcoyne et al. | |
| 2004/0249293 A1 | 12/2004 | Sandler et al. | |
| 2005/0165317 A1 | 7/2005 | Turner et al. | |
| 2005/0210988 A1 | 9/2005 | Amano et al. | |
| 2005/0277839 A1 | 12/2005 | Alderman et al. | |
| 2006/0020239 A1 | 1/2006 | Geiger et al. | |
| 2006/0074479 A1 | 4/2006 | Bailey et al. | |
| 2006/0079782 A1 | 4/2006 | Beach et al. | |
| 2007/0255357 A1 | 11/2007 | Rose et al. | |
| 2008/0033527 A1 | 2/2008 | Nunez et al. | |
| 2008/0050830 A1 | 2/2008 | Floriano et al. | |
| 2008/0081965 A1 | 4/2008 | Edman et al. | |
| 2008/0108930 A1 | 5/2008 | Weitzel et al. | |
| 2008/0278336 A1 | 11/2008 | Ortega et al. | |
| 2009/0024041 A1 | 1/2009 | Cho et al. | |
| 2009/0054737 A1 | 2/2009 | Magar et al. | |
| 2009/0088612 A1 * | 4/2009 | Bouton | A61M 1/3653 604/4.01 |
| 2009/0131767 A1 | 5/2009 | Arne et al. | |
| 2009/0215072 A1 | 8/2009 | McDevitt et al. | |
| 2009/0295383 A1 | 12/2009 | Gianchandani et al. | |
| 2010/0049004 A1 * | 2/2010 | Edman | A61B 5/4869 600/300 |
| 2010/0130864 A1 * | 5/2010 | Donnelly | A61B 8/14 382/128 |
| 2011/0021902 A1 * | 1/2011 | Kim | A61B 5/333 600/523 |
| 2011/0054333 A1 | 3/2011 | Hoffer | |
| 2011/0071482 A1 * | 3/2011 | Selevan | G04F 3/08 604/304 |
| 2011/0301882 A1 | 12/2011 | Andersen | |
| 2011/0313261 A1 | 12/2011 | Bourget et al. | |
| 2013/0030259 A1 | 1/2013 | Thomsen et al. | |
| 2013/0060098 A1 | 3/2013 | Thomsen et al. | |
| 2013/0331919 A1 | 12/2013 | Zhang et al. | |
| 2014/0100432 A1 | 4/2014 | Golda et al. | |

(56) References Cited

U.S. PATENT DOCUMENTS

| | | | |
|---|---|---|---|
| 2014/0107452 A1* | 4/2014 | Wu | A61B 5/24 600/372 |
| 2014/0266776 A1 | 9/2014 | Miller et al. | |
| 2014/0316289 A1 | 10/2014 | Kassab | |
| 2015/0011412 A1 | 1/2015 | Deirmengian et al. | |
| 2015/0018643 A1 | 1/2015 | Cole et al. | |
| 2015/0025394 A1 | 1/2015 | Hong et al. | |
| 2015/0031049 A1 | 1/2015 | Kentsis et al. | |
| 2015/0157262 A1 | 6/2015 | Schuessler et al. | |
| 2015/0164372 A1 | 6/2015 | Navab et al. | |
| 2015/0164592 A1 | 6/2015 | Elhawary et al. | |
| 2015/0292856 A1 | 10/2015 | Ganton et al. | |
| 2015/0320357 A1 | 11/2015 | Kuraguntla et al. | |
| 2015/0366530 A1 | 12/2015 | Ku | |
| 2016/0112775 A1 | 4/2016 | Kim et al. | |
| 2016/0153878 A1 | 6/2016 | Candon et al. | |
| 2016/0183794 A1 | 6/2016 | Gannon et al. | |
| 2016/0198961 A1 | 7/2016 | Homyk et al. | |
| 2016/0256107 A1 | 9/2016 | Gupta et al. | |
| 2016/0262670 A1 | 9/2016 | Wasson et al. | |
| 2016/0287177 A1 | 10/2016 | Huppert et al. | |
| 2016/0331313 A1 | 11/2016 | Kuraguntla et al. | |
| 2016/0367155 A1 | 12/2016 | Barrett et al. | |
| 2017/0014572 A1 | 1/2017 | Newberry et al. | |
| 2017/0055845 A1 | 3/2017 | Mirov et al. | |
| 2017/0180870 A1* | 6/2017 | Hung | A61B 7/00 |
| 2017/0293846 A1 | 10/2017 | Zyglowicz et al. | |
| 2018/0014787 A1 | 1/2018 | Ganton et al. | |
| 2018/0070841 A1* | 3/2018 | Honore | A61B 5/02007 |
| 2018/0250463 A1 | 9/2018 | Olivarez | |
| 2020/0330011 A1* | 10/2020 | Honore | A61B 5/1455 |
| 2021/0212616 A1* | 7/2021 | Honore | A61B 5/0261 |

FOREIGN PATENT DOCUMENTS

| | | |
|---|---|---|
| WO | WO-9942039 A1 | 8/1999 |
| WO | WO-0200118 A2 | 1/2002 |
| WO | WO-2006086435 A2 | 8/2006 |
| WO | WO-2008006003 A2 | 1/2008 |
| WO | WO-2010036930 A1 | 4/2010 |
| WO | WO-2014100795 A1 | 6/2014 |
| WO | WO-2014117037 A1 | 7/2014 |
| WO | WO-2015126703 A1 | 8/2015 |
| WO | WO-2016110804 A1 | 7/2016 |
| WO | WO-2016144812 A1 | 9/2016 |
| WO | WO-2016145001 A1 | 9/2016 |
| WO | WO-2017027643 A1 | 2/2017 |
| WO | WO-2018013725 | 1/2018 |
| WO | WO-2018049412 | 3/2018 |
| WO | WO-2018183558 A1 | 10/2018 |
| WO | WO-2019055520 A1 | 3/2019 |

OTHER PUBLICATIONS

Gupta, et al. Use of a piezoelectric film sensor for monitoring vascular grafts. Am J Surg. Aug. 1990;160(2):182-5; discussion 185-6.

International search report and written opinion dated Apr. 14, 2014 for PCT/US2014/013068.

International search report and written opinion dated May 14, 2015 for PCT/US2015/015502.

International Search Report and Written Opinion dated May 19, 2016 for International PCT Patent Application No. PCT/US2016/021026.

International Search Report and Written Opinion dated May 26, 2016 for International PCT Patent Application No. PCT/US16/21441.

International Search Report and Written Opinion dated Nov. 17, 2017 for International PCT Patent Application No. PCT/US2017/051213.

Kistler, et al. The bruit of carotid stenosis versus radiated basal heart murmurs. Differentiation by phonoangiography. Circulation. May 1978; 57(5):975-81.

Knox, et al. Quantitative Carotid Phonoangiography. Stroke. Nov.-Dec. 1981;12(6):798-803.

Neville, et al. An expanded series of distal bypass using the distal vein patch technique to improve prosthetic graft performance in critical limb ischemia. Eur J Vasc Endovasc Surg. Aug. 2012;44(2):177-82. doi: 10.1016/j.ejvs.2012.04.014. Epub May 15, 2012.

Notice of Allowance dated Jan. 10, 2018 for U.S. Appl. No. 15/064,318.

Notice of Allowance dated Jun. 8, 2016 for U.S. Appl. No. 14/163,991.

Notice of Allowance dated Nov. 15, 2017 for U.S. Appl. No. 15/064,318.

Office Action dated Jan. 5, 2016 for U.S. Appl. No. 14/163,991.

Office Action dated Jan. 22, 2019 for U.S. Appl. No. 15/702,390.

Office Action dated Jan. 26, 2018 for U.S. Appl. No. 14/619,948.

Office Action dated May 22, 2019 for U.S. Appl. No. 15/220,222.

Office Action dated May 22, 2019 for U.S. Appl. No. 15/220,226.

Office Action dated Jul. 13, 2018 for U.S. Appl. No. 15/220,226.

Office Action dated Jul. 25, 2018 for U.S. Appl. No. 15/220,222.

Office Action dated Sep. 22, 2017 for U.S. Appl. No. 14/619,948.

Office Action dated Nov. 12, 2019 for U.S. Appl. No. 15/702,390.

Park, J. et al. A Wireless Pressure Sensor Integrated with a Biodegradable Polymer Stent for Biomedical Applications. Sensors (Basel). Jun. 2, 2016;16(6).

PCT/US2017/041773 Intentional Search Report dated Sep. 26, 2017.

PCT/US2018/024925 International Search Report dated Jul. 26, 2018. 5 Pages.

PCT/US2018/024925 Written Opinion dated Jul. 26, 2018. 11 Pages.

Tsagakis, et al. Overall Essen's experience with the E-vita open hybrid stent graft system and evolution of the surgical technique. Ann Cardiothorac Surg. Sep. 2013;2(5):612-20. doi: 10.3978/j.issn.2225-319X.2013.09.17.

U.S. Appl. No. 15/064,318 Notice of Allowance dated Feb. 9, 2018.

U.S. Appl. No. 15/702,390 Notice of Allowance dated Mar. 22, 2022.

U.S. Appl. No. 15/702,390 Notice of Allowance dated Mar. 31, 2022.

U.S. Appl. No. 15/702,390 Office Action dated Dec. 10, 2021.

U.S. Appl. No. 15/702,390 Office Action dated Mar. 17, 2020.

U.S. Appl. No. 15/702,390 Office Action dated May 14, 2021.

U.S. Appl. No. 15/702,390 Office Action dated Sep. 14, 2020.

\* cited by examiner

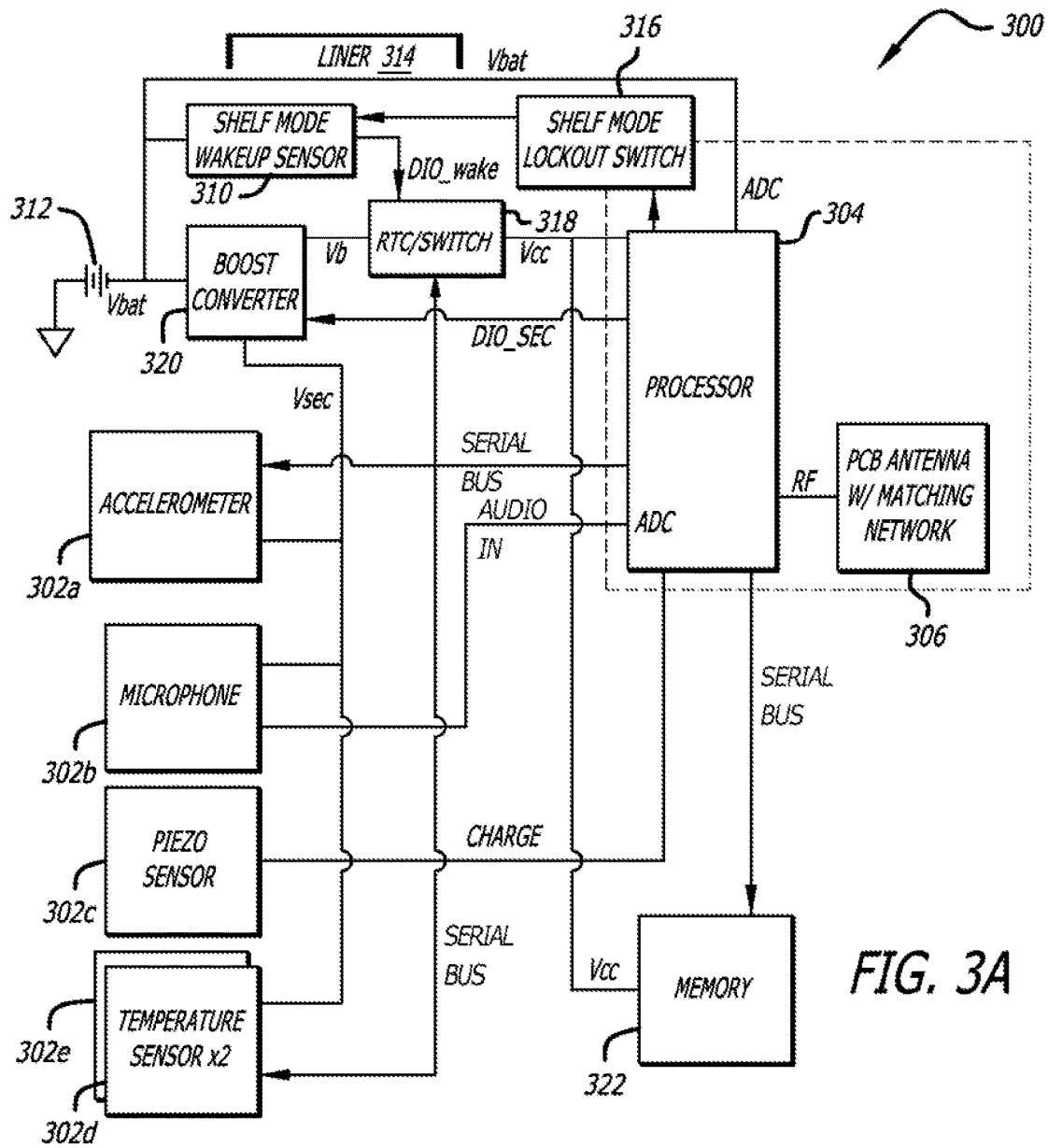
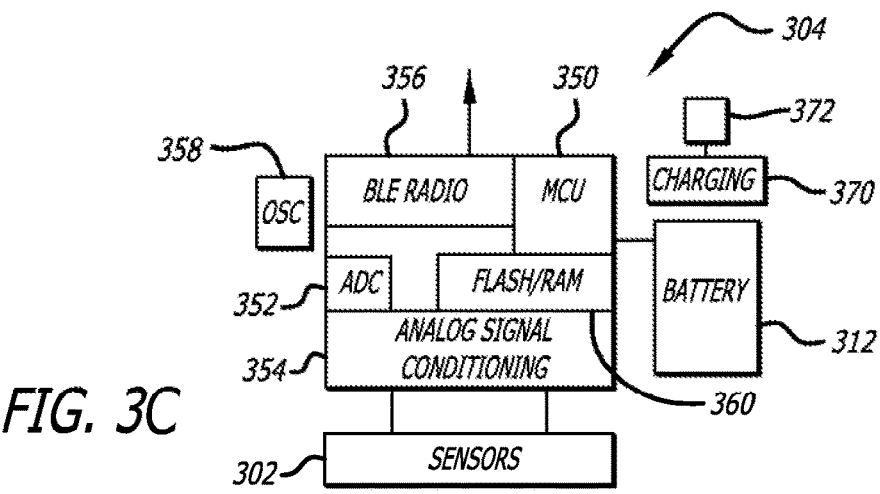
*FIG. 3A*
*FIG. 3C*

WEARABLE DEVICE WITH MULTIMODAL DIAGNOSTICS

CROSS-REFERENCE

This application is a continuation of U.S. patent application Ser. No. 15/702,390, filed Sep. 12, 2017, which claims priority to U.S. Provisional Application No. 62/393,590, filed on Sep. 12, 2016, the entire contents of which are incorporated herein by reference in its entireties.

BACKGROUND OF THE INVENTION

1. Field of the Invention. The present invention relates to methods and systems using sensors to non-invasively measure subcutaneous processes in a patient, and more particularly to systems and methods for simultaneously measuring a plurality of sensory modalities and processing the measurements to detect physiological phenomenon in the patient's body.

Stethoscopes are effective tools used in the hospital and doctor's office during physical exams for noninvasive detection of physiologic sounds. Several designs have gained popularity amongst clinicians, such as the Littmann™ stethoscope, and the Welch-Allyn™ stethoscope. These devices have been designed to be portable devices that are clinician-centric and can be easily be moved from one location to another on a patient during a single visit, and also easily used across several patients. Physiological issues such as blocked blood flow, abnormal lung sounds, heart murmurs, etc. occur at specific locations on the body (e.g. the arm for a blocked arteriovenous fistula, the neck for an obstruction in the carotid artery, the chest or back for abnormal air flow in the lungs, etc.) and are typically detectable using stethoscopes during patient-doctor exams. These physiological issues cannot however be effectively tracked outside of the clinic. The stethoscope requires the patient's presence in the clinic to be used by a doctor trained in interpreting the noise heard on the stethoscope. This makes management of patients more difficult and leads to poor patient outcomes, since the patient cannot be monitored for a developing health issue until it has caused the patient damage.

One application that illustrates the limitations of a stethoscope is the monitoring of the flow rate of an arteriovenous access, such as for example an arteriovenous access used with patients undergoing dialysis. Dialysis patients may have a fistula (natural vein) or a synthetic graft inserted to provide access to blood flow for dialysis treatments. An example of how access to blood flow in a dialysis patient may be achieved is illustrated in FIG. 1. FIG. 1 is an image of a patient's arm 100 with selected veins and arteries fitted with an arteriovenous (AV) access 102. The AV access 102, which in the illustrated example is implemented using a synthetic bridge graft, is inserted to receive blood from an artery 104. The AV access 102 extends from the artery 104 to a vein and thereby transports blood to the vein 106. A first catheter 108 is inserted into the AV access 102 on the arterial side to transport some of the blood (at 109) from the artery 104 to a dialysis machine (not shown). A second catheter 110 is inserted on a venous side to transport the blood (at 111) from the dialysis machine back into the vein 106. Over time, the AV access 102 may become occluded and prevent the patient from receiving dialysis treatment. The blockage can typically be acute as the result of thrombosis or build up over time through stenosis. A blockage can also be the result of narrowing caused by stenosis which can lead to a thrombosis.

A blockage detected sufficiently early may be treated. The AV access may be unclogged (e.g. by performing a thrombectomy or angioplasty) while preserving the access. If a thrombosis forms, clinicians must intervene prior to the hardening of the thrombus, which typically occurs within 48-72 hours, in order to successfully treat the patient and preserve the access. If left untreated, the access may need to be replaced, which may lead to 4-12 weeks of catheter-based dialysis in the patient's treatment. Central catheters carry several well-known risk factors for patients (e.g. infection, easily blocked, etc.) and as a result, their long-term inclusion in a patient's dialysis protocol is considered to be an indicator of poor quality of care for the dialysis patient by organizations such as the Center for Medicare Services (CMS) and the National Kidney Foundation. A stethoscope may be used to detect a thrombosis sufficiently early to treat and preserve the access. However, the stethoscope is only available to detect the thrombosis when the patient is in the presence of a doctor that has it. A thrombosis may harden during the time between such occasions.

There is a need in the art for a device and system that provides the ability to automatically collect, store, transmit and process sensor data several times a day while not requiring patient action for any of the above steps. There is also a need in the art for a device and system that provides the ability to identify a problematic signal and alert a clinician about bringing the patient in for a more thorough examination.

It would also be advantageous for noninvasive methods and devices that may be used to monitor physiological phenomenon to be wearable by the patient. Existing stethoscope designs today are ill-suited to meet a wearable form factor. Stethoscopes are designed as rigid devices that would be unwieldy to leave on a patient for any length of time due to their dimensions and weight. These devices are also necessarily rigid due to their underlying architecture. Stethoscopes often have a "cup" or other form of diaphragm that is used to provide acoustic impedance matching from the skin to another medium. These components add to the overall bulk and rigidity of existing stethoscopes. The bulk and rigidity of existing stethoscopes does add to the ease of use for these devices in their classic use case, typically, a clinician moving the stethoscope from one location to another easily to perform a complete physical examination on a patient during their visit. However, this removes them as practical devices that could be used as a long-term, low-profile wearable device for remote monitoring of patient health.

The stethoscope is also limited to detecting a single sensory modality. The doctor listens for sounds that indicate blocked blood flow, abnormal lung sounds, heart murmurs, for example. It would be advantageous for a wearable device to be used in a variety of other applications, including but not limited to detection of anomalous beat patterns in the heart, abnormal flow through a vessel, or abnormal breathing patterns/air flow in the lungs. Continuous monitoring in diverse locations would also be advantageous.

BRIEF SUMMARY OF THE INVENTION

In view of the above, devices, systems and methods are provided to automatically collect, store, transmit and process sensor data several times a day while not requiring patient action for any of the above steps. The devices, systems and methods may also identify a problematic signal and alert a clinician about bringing the patient in for a more thorough examination.

In one example implementation, a wearable patch is provided for sensing information relating to subcutaneous processes in a patient. The wearable patch includes a patch substrate configured to attach to a body part of a patient. A sensor assembly is mounted on the patch substrate. The sensor assembly comprises a plurality of sensors configured to detect a corresponding plurality of sensory modalities and generates electrical signals representing the sensory modalities. A signal converter on the wearable patch is configured to receive the electrical signals from the plurality of sensors and to convert the signals to sensor data signals comprising a data representation of at least one of the electrical signals. A communications interface communicates the sensor data signals to a sensor data processing system.

In another example implementation, the device is implemented in a system that includes a sensor data processing system.

In another example implementation, a method is provided for monitoring subcutaneous processes in a patient. The method includes sensing a plurality of sensory modalities using a sensor assembly comprising a plurality of sensors mounted on a wearable patch. The sensory modalities are received as electrical signals representing the sensory modalities. The electrical signals are converted to a plurality of corresponding sensor data signals. The sensor data signals are then transmitted to a sensor data processing system.

Some examples of devices, systems, and methods for automatically collecting, storing, transmitting and processing sensor data are outlined above rather broadly in order that the detailed description thereof may be better understood, and in order that the present contribution to the art may be better appreciated. Additional example implementations of the devices, systems, and methods are described below and will form the subject matter of the claims appended hereto. In this respect, before explaining at least one example of the devices, systems, and methods in detail, it is to be understood that the devices, systems, and methods are not limited in their application to the details of construction or to the arrangements of the components set forth in the following description or illustrated in the drawings. Other example implementations of the devices, systems, and methods may be developed, practiced and carried out in various ways. Also, it is to be understood that the phraseology and terminology employed herein are for the purpose of the description and should not be regarded as limiting.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 3A is a block diagram of another example implementation of a wearable patch with a sensor assembly and a wireless communication interface.

FIG. 3C is a block diagram of an example of a processor used in example implementations of the wearable patch in FIG. 3A.

DETAILED DESCRIPTION OF THE INVENTION

Figure 1:
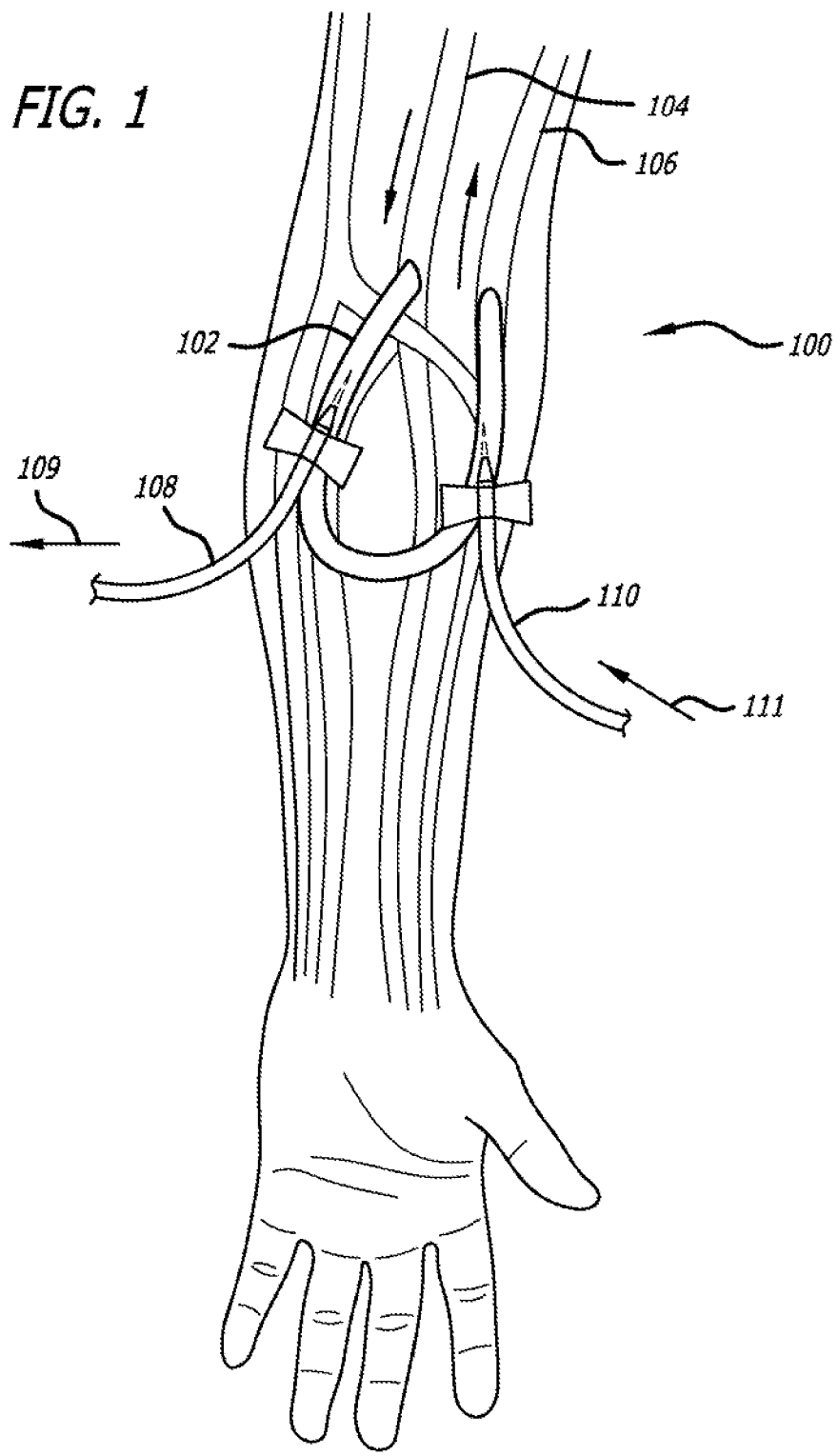
FIG. 1 depicts an arm having a synthetic bridge graft between an artery and a vein.

System Description.

Disclosed herein are systems and methods for monitoring a patient. In an example implementation, a system for monitoring a patient includes a wearable device, or a wearable patch, configured to attach to a body part of a patient. The wearable patch incudes a sensor assembly mounted on a patch substrate (described below with reference to FIGS. 4A and 4B), which is the portion that physically attaches to the patient. The sensor assembly comprises a plurality of sensors configured to detect a corresponding plurality of sensory modalities and generate electrical signals representing the sensory modalities. The wearable patch includes a signal converter configured to receive the electrical signals from the plurality of sensors and to convert the signals to sensor data signals comprising a data representation of at least one of the electrical signals. The patch may include a storage mechanism (memory local to the patch) to retain the sensor data signals until a communications interface can be established. A communications interface communicates the sensor data signals to a sensor data processing system. The signal converter and the communications interface may also be mounted on the wearable patch portion with the sensor assembly. The wearable patch portion of the wearable patch is attached to a patient to take measurements based on the sensors included in the sensor assembly. The data from the sensors is communicated to the sensor data processing system.

As used herein, the terms "close proximity," "local," "locally," "substantially close," or "near" in reference to a patient wearing a wearable device or patch shall mean within a distance at which the communication interface on the wearable patch communicates using Bluetooth™, Near-Field Communication (NFC), near field magnetic communication, a wired connection, or any wireless technology adapted for short or medium range communication. Communications over distances typically by cellular, WiFi to the Internet, the Internet, satellite, or any other technology configured for communication beyond a building shall be understood to be "remote," "far," or at a "long distance."

In an example implementation, the communication interface on the wearable patch transmits sensor data signals, processed measurements, or alerts indicating that more thorough examination of the patient may be required, to a local hub using a first protocol configured for local or near distance communications. The local hub communicates the sensor data signals to a remote sensor data processor over a second protocol configured for long distance communication. The first protocol may include Bluetooth™, near field communication protocols, near field magnetic protocols, or any communication protocol configured to provide communications over a short distance. The second protocol may include cellular communications, WiFi communication via the Internet, satellite communications, and other long distance communications protocols. In the second protocol, a local hub is not required. In one example, a local hub may be implemented as an application on a smartphone using Bluetooth™ to receive sensor data signals from the wearable patch. The wearable patch and the smartphone may process the sensor data signals to a desired extent, or may simply relay the sensor data signals to the remote sensor data processor using a WiFi connection to the Internet or a cellular data connection.

It is noted that in some example implementations, the local hub is not used and the communication interface on the patch may connect directly to the Internet to a cloud service, a database, or other system that may include a remote sensor data processor. In such implementations, the communications interface on the patch may implement a communication protocol suitable for connecting to the Internet or other data network, such as for example, a WiFi protocol, a cellular data communications protocol, satellite communications or any other long distance communication protocols.

The sensor data processing system, which may include the local hub and the remote sensor data processor may include an interface to a patient medical records database, any suitable database, or a web portal. The sensor data processing system may also include an alerting system to send notifications of conditions requiring urgent attention to a doctor or any other specified person. The notifications may be sent using any suitable communications system such as, for example, notification via e-mail, notification on a website, notification by text message, or any other suitable signaling mechanism.

The sensor assembly on the patch substrate may include any combination of sensors. For example, sensors included in example implementations of the sensor assembly may include any combination of the following:
 1. acoustic sensors
 2. inertial sensors (including accelerometers, gyroscopes, angular accelerometer, etc.)
 3. strain gauges
 4. temperature sensors
 5. pressure sensors
 6. optical sensors
 7. moisture sensors
 8. conductivity sensors
 9. chemical sensors
 10. flow sensors In some implementations, an ultrasonic transducer may be disposed in the sensor assembly along with ultrasonic sensors to obtain ultrasonic imaging of a desired body part.

In some implementations, the sensor assembly may be configured for specific applications by selecting sensors that provide information that may be used to determine a state of a certain condition. In one example, the wearable patch may be configured to monitor an arteriovenous (AV) fistula on a dialysis patient. The wearable patch may include a sensor assembly having an acoustic sensor, an accelerometer, a strain gauge, and two thermometers. The acoustic sensor may be a microphone designed to have a flat sensitivity between about 20 Hz and 10 kHz, or at least a range that is substantially equivalent to that of human hearing. The accelerometer may be selected to be sensitive along three axes from DC to 500 Hz. The strain gauge may be selected to have a sensitivity to mechanical strain between 0.1 Hz to 20 MHz. The temperature sensors may be selected to have resolutions below 0.1° C. and sample up to 8 Hz.

In the example application, the wearable patch may be applied to the surface of a patient's arm over an AV fistula, which may be used for kidney dialysis. FIG. 1 depicts an arm having a synthetic bridge graft used as an AV fistula between an artery and a vein. The output of the microphone provides an acoustic signature of the flow within the fistula. The accelerometer provides several pieces of information. For example, the accelerometer generates data indicative of the orientation of the arm with respect to gravity from the DC component of all three axes. The accelerometer may also be used to determine if the arm is in motion during the reading of the data, which in turn may be used to determine if the motion of the arm was sufficient to affect the readings from the other sensors. The accelerometer may also provide a ballistic cardiographic measurement in the location of the fistula. The strain gauge provides information about the strength of the pressure wave through the fistula as it forces expansion on the surface of the skin. The two temperature sensors provide a differential measurement of skin temperature in the region of the fistula relative to a location without significant arterial flow. Thermography is well-known as a tool for determining the state of healthy blood flow in the periphery.

The sensor assembly fitted with the above-described sensors provides multiple and simultaneously collected data streams at any given time. The combination of these simultaneous data streams provides a more complete and accurate assessment of the quality of blood flow within the fistula, more than any single data stream can provide individually. The specific signature of the multiple data streams processed together can provide diagnostic information to the clinician as to the source of any change in the condition of the fistula.

Figure 2:
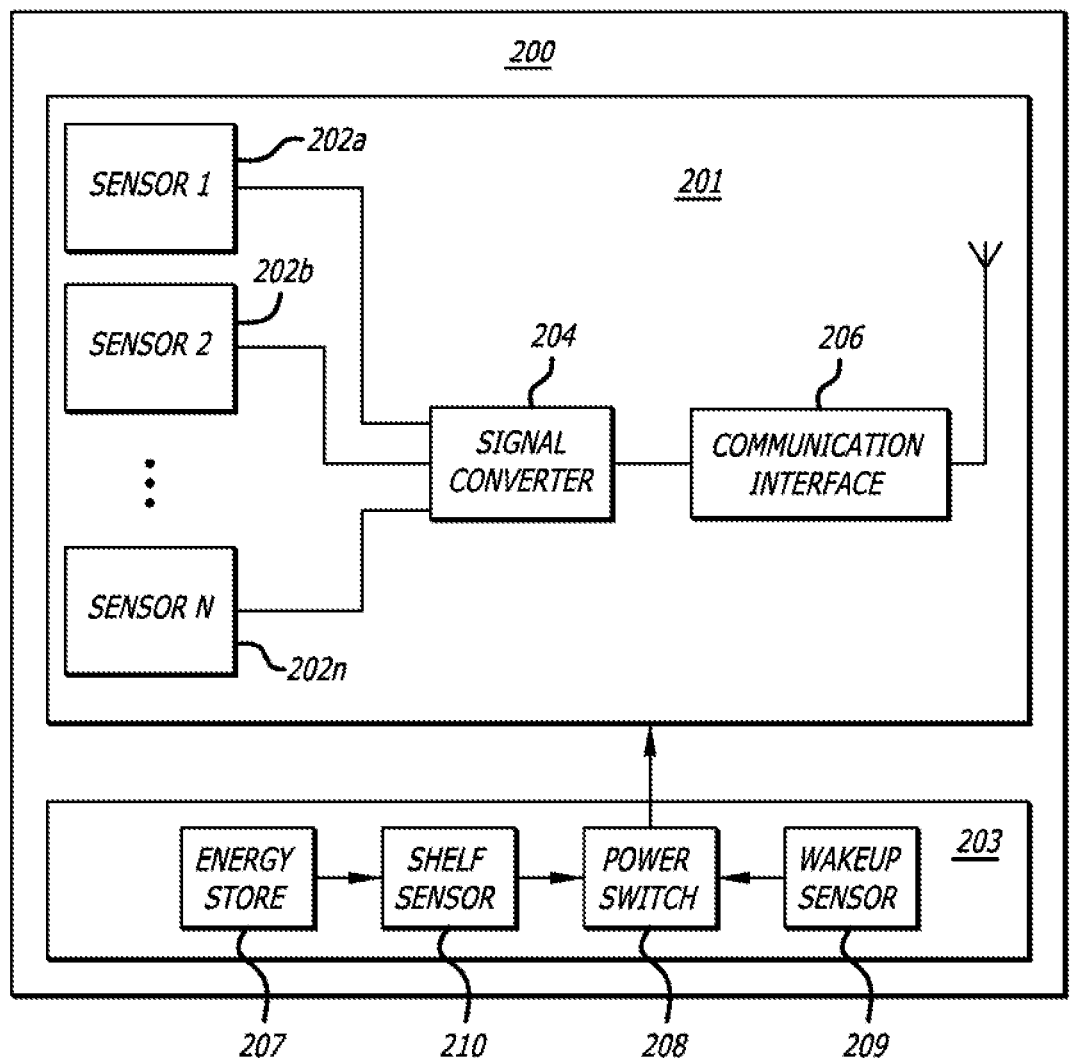
FIG. 2 is a block diagram of an example implementation of a wearable patch with a sensor assembly and a wireless communication interface.

FIG. 2 is a block diagram of an example implementation of a wearable patch 200 comprising a sensor control module 201 and a power module 203. It is noted that the block diagram in FIG. 2 is schematic such that components are described in functional bocks for clarity with no intent to limit the described examples to any number of modules. An example implementation may include separate hardware modules implementing the sensor control module 201 and the power module 203. In other implementations, a single hardware module, e.g. a circuit board, may include components of both the sensor control module 201 and the power module 203.

The sensor control module 201 includes a sensor assembly 202 and a wireless communication interface 206. The sensor assembly 202 includes N sensors, sensor 1 202a, sensor 2, 202b, and additional sensors up to sensor N 202n. Each sensor 202a-n detects a corresponding sensory modality and converts the sensory modality to an electrical signal. The electrical signal is communicated to a signal converter to convert the electrical signal to a suitable data representation of the properties indicated by the electrical signal. For example, the acoustic sensor may be a microphone or a piezoelectric transducer. Sound is converted to electrical signals in a well-known manner producing a signal having a frequency and an amplitude. The electrical signal may be processed by amplifying the signal and filtering the signal to reduce any noise that may be in the signal. The electrical signal may then be input to a signal converter 204 to convert the electrical signal to data.

The signal converter 202 may include an analog-to-digital converter (ADC) to generate a series of digital samples representing a voltage level at each part of a wave formed by the electrical signal. The signal converter 204 may also include a processor to perform, for example, digital signal processing techniques to either reduce the data set to include only the most meaningful data, to filter out signal anomalies, or to perform other similar functions. The processor may also include functions to manage the operation of the wearable patch 200. For example, the processor may be programmed to implement an operating system, such as for example, a state machine in which the components are controlled according to various states. Other types of operating systems may also be used, such as an infinite loop of control functions for acquiring sensor data, and managing the power during times in which the wearable patch is not acquiring sensor data. The processor may operate using interrupt schemes, or polling of input/output (I/O) devices to control the functions of the wearable patch 200. The processor may be programmed to perform minimal processing of the data, or to perform signal conditioning functions or to perform more high-level functions such as analysis sufficient to determine if an alert should be communicated. In some implementations, the digital signal processing and other high-level functions may be performed by the sensor data processing system, which may be at the local hub in a system that includes the local hub.

Each sensor 202 may be connected to provide electrical signals to the signal converter 204 to form channels of sensor data. The signal converter 204 may be configured to provide signal processing functions tailored to the sensor 202 connected to the signal converter 204. The signal converter 204 may also include functions to format the simultaneously collected data as a sensor data signal in a manner that permits the sensor data signal to be communicated. The signal converter 204 communicates the sensor data signal to the communication interface 206 for transmission to the sensor data processing system. In some implementations, the sensor data may be combined into a single sensor data signal. In other implementations, the sensor data may be formatted in sensor data signals that correspond to each sensor from which the data is obtained. That is, the sensor data signal may be communicated as a single data stream that combines the sensor data from each sensor, or as multiple data streams each having the sensor data from a corresponding sensor. The sensor data may be may be stored in a memory device prior to communicating the sensor data over a data network. In some cases, the sensor data may be collected while a connection via the communications interface is unavailable. The sensor data may then be stored until a connection via the communications interface is available. The sensor data may be compressed for more efficient storage and transmission.

The communication interface 206 may be configured to operate using any suitable communications protocol. A wireless communication protocol is preferred, although a wired communication protocol may be used as well. In an example implementation in which the wearable patch 200 communicates with a local hub, which then communicates with a remote sensor data processor, the communication interface 206 may include functions enabling communication using communication protocols for short distance communication. The communications interface 206 may also communicate using communication protocols for short distance communication to transmit sensor data signals to a locally placed sensor data processing system. The system data processing system may provide monitoring functions, diagnostic functions, and may interface with locally or remotely located databases or web portals. The system data processing system may also include functions to send alerts by email, text messages, or other available formats.

The power module 203 includes an energy source 207 such as, for example, a battery or other portable energy source that may be of limited capacity. The power module 203 may be configured to operate in a low power state. In an example implementation, the power module 203 may be configured to operate in a state in which the components on the sensor control module 201 are isolated from the energy source 207 be a power switch 208 as shown in FIG. 2. The low power state, or the state in which power is switched off permit the wearable patch to implement functions that conserve energy.

In an example implementation, the power module 203 may include a wakeup sensor 209 to change the state of the power switch 208 after a period of time. The power to the sensor control module 201 may be turned off during the time period and then turned on to power the sensor module 201 after the time period has elapsed. The wakeup sensor 209 implements a power-on, power-off cycle so that the sensor control module 201 only uses power when it is needed. The wearable patch does not need to read and process data from the sensors continuously because the parameters analyzed from the sensor data change over periods of time that are much greater than the frequency at which sensor data can be collected. Power can be saved by turning the power off when the wearable patch does not need to be performing any functions.

The wakeup sensor 209 may be implemented using a watchdog timer that times up, or down, to, or from a time period. When the time period elapses, the watchdog timer may switch the power switch 208 to power the sensor control module 201 and to signal the processor to perform needed functions, such as acquisition of sensor data, or other processing functions. In example implementations, the wakeup sensor 209 may include a sensor that detects activity at one or more of the sensors 202a-202n. For example, the wakeup sensor 209 may include a signal detecting function in which an electrical signal from one or more sensors of sufficient magnitude to constitute a meaningful signal from the sensors is detected as a trigger to power the signal control module 201 to begin acquisition.

In some implementations, the wakeup sensor 209 may be a sensor of selected states that indicate conditions for which power should be provided to the signal control module 201. For example, the wakeup sensor 209 may include any combination of the following:

1. Magnetic sensors or switches
2. Optical sensors
3. Motion, acceleration or tilt sensors
4. Temperature sensors
5. Capacitive proximity sensors
6. Mechanical switches The above types of sensors may be used in example implementations as the wakeup sensor 209 in a variety of ways depending on the modality of the sensor. For example, a mechanical switch may be used as a simple power on/power off button to activate the wearable patch 200. Temperature sensors and motion sensors (e.g. accelerometers) may be used to trigger the wearable patch 200 into an active, power-on state based on selected conditions of the patient. Magnetic sensors/switches, capacitive proximity sensors, and optical sensors may be configured to trigger to a power-on state based on environmental conditions, which may include specific signals provided to turn the wearable patch 200 to a power-on state by another mechanism.

The wearable patch 200 may also include functions and components to support long term storage of the wearable patch 200 while conserving power without the need for a switch to turn the power to the wearable patch 200 to the on-state. For example, the wearable patch 200 may operate in a "shelf mode." The shelf mode may be entered via explicit control (e.g. a command) received from a device communicating over the communication interface 206. In some implementations, the shelf mode may be entered based on one of the sensors 202. In some implementations, the shelf mode may be entered based on a specific shelf sensor 210 as shown in FIG. 2. When in shelf mode, the various components of the wearable patch 200 may be commanded to enter a low power mode, or may be cut off from power by the power switch 208, or other switches selectively inserted to control selected sensors 202. The shelf mode can be exited based on any of the sensors 202 (e.g. when starting to receive sensor signals), or via the optionally implemented shelf sensor 210. The shelf sensor 210 may be configured to automatically detect when the wearable patch 200 is being deployed, or when the wearable patch 200 is to be attached to a patient for service. The shelf sensor 210 may be implemented using any one of, or any combination of the following:

1. Magnetic sensors or switches
2. Optical sensors
3. Motion, acceleration or tilt sensors
4. Temperature sensors
5. Capacitive proximity sensors
6. Mechanical switches In example implementations, the shelf sensor 210 interacts with the packaging 200 in which the wearable patch is stored prior to deployment on a patient. When the wearable patch 200 is in its packaging, the wearable patch 200 is in shelf mode, which means that the shelf sensor 210 operates to preclude a power connection from the energy source 207 to the sensor control module 201. In some implementations, the packaging may be configured to generate a magnetic field and the shelf sensor 210 may be implemented using a magnetic sensor to detect the magnetic field while in its packaging. For example, the packaging may include an envelope or similar container made of a material capable of generating a magnetic field. Examples of such a material include paper, plastic, other similar material impregnated with magnetic particles. In other examples, a magnetic material may be formed as a laminate or a layer attached to the material forming the container of the wearable patch 200. The sensor control module 201 may be configured to prevent the wearable patch 200 from being activated (i.e. in a power-off state) and thereby consuming power when the shelf sensor 210 senses the magnetic field while the wearable patch 200 is enclosed in its packaging. When the wearable patch 200 is removed from its packaging for deployment, and the magnetic field is no longer sensed by the shelf sensor 210, which then switches states to trigger the power switch 208 to turn power on to the sensor control module 201.

In another example implementation, the wearable patch 200 may be provided with an applicator component during manufacturing. The applicator component may be an adhesive backing liner made of paper, plastic, nylon, or other suitable material that may be removably attached to the adhesive surface of the wearable patch 200. The adhesive backing liner is configured so that a user would remove the adhesive liner during application of the wearable patch 200 on the patient. The adhesive backing liner may be made of a material containing a magnetic component that generates a magnetic field. When the magnetic adhesive backing liner is removed to apply the wearable patch 200 on the patient, the magnetic field is removed as well so that the shelf sensor 210 (implemented as a magnetic sensor) can no longer detect the magnetic field. When the magnetic field is no longer detected, the wearable patch 200 is taken out of shelf mode and the shelf sensor 210 triggers or enables the power switch 208 to allow the energy source 207 to power the sensor control module 201.

In other example implementations, the packaging may be opaque to light and the shelf sensor 210 may be an optical sensor. In one implementation, the wearable patch 200 may be enclosed in a packaging enclosure that is opaque. When the wearable patch 200 is enclosed in its packaging, the shelf sensor 210 implemented using an optical sensor would not detect light and would keep the wearable patch 200 in the shelf mode precluding the energy source 207 from powering the sensor control module 201. When the wearable patch 200 is removed from the packaging, the shelf sensor 210 implemented as an optical sensor would be exposed to ambient light allowing the shelf sensor 210 to sense the ambient light. The shelf sensor 210 implemented as an optical sensor would then emit an electrical signal indicating that the wearable patch 200 is no longer in a shelf mode thereby enabling the delivery of power to the sensor control module 201.

In another implementation in which the shelf sensor 210 is implemented using an optical sensor, the wearable patch 200 may include an opaque applicator component such as an adhesive backing liner that is used to facilitate application of the wearable patch 200 to the patient. The opaque applicator component may cover the shelf sensor 210 (implemented as an optical sensor) while in storage until the applicator component is removed from the wearable patch 200 during deployment of the wearable patch 200.

Example Implementation of a Wearable Patch

FIG. 3A is a block diagram of another example implementation of a wearable patch 300 with a sensor assembly 302 and a wireless communication interface 306. The wearable patch 300 in FIG. 3A includes a sensor assembly comprising an accelerometer 302a, a microphone 302b, a piezoelectric sensor 302c, and two temperature sensors (a first temperature sensor 302d and a second temperature sensor 302e). It is noted that FIG. 3A depicts one example combination of sensors that may be deployed in the sensor assembly 302. The sensor assembly 302 may include different combinations of sensors 302 that may correspond to different applications. Sensor assemblies may also be provided with multiple sensing modalities that may be tailored to the needs of different patients.

It is assumed in the example described below that the wearable patch communicates to a local hub, which then communicates data to a remote sensor data processor. In some example implementations as mentioned above, the wearable patch may communicate with a remote sensor data processor without communicating first to a hub, such as by WiFi, cellular or other communications technologies.

The sensors 302 in FIG. 3A are connected to communicate with a processor 304, which may include ADC functionality and other signal conditioning functions. The processor 304 converts the electrical signals from each sensor to sensor data signals for communication via the communication interface 306.

The wearable patch 300 in FIG. 3A is one example implementation of a wearable device for simultaneously obtaining data from multiple sensory modalities detected using multiple sensors. The operation of the wearable patch 300 in FIG. 3A is described as follows. Those of ordinary skill in the art understand the implementation details described below are provided as examples, and are also able to identify and use alternatives.

The example wearable patch 300 in FIG. 3A may be configured, in accordance with an example processor 304 to capture data from several analog channels and from devices connected over a serial bus, such as for example, an inter-integrated circuit (I2C) bus, an SPI bus, or any other suitable serial interconnection. One channel may be used to communicate electrical signals representing sound from the microphone 302b. The remaining channels correspond to the accelerometer 302a, the two temperature sensors 302d, 302e communicating over the I2C bus. A channel may be configured as a charge-amplified channel for piezo sensing by the piezo sensor 302c.

It is noted that the example in FIG. 3A implements serial bus interconnections, however, parallel interconnections or buses can be used as well depending on the requirements of specific implementations.

Sensor Read Process

The processor 304 may control the sensor assembly 302 by, for example, controlling the collection of data from the sensors. Signals from the sensors may be collected for a predetermined read duration time (such as for example, 5 seconds) on the corresponding channels. Signals from the temperature sensors may be detected once at the beginning of the sensor signal measurement period. Audio input from the microphone 302b may be sampled by an ADC using, for example, the ADC function on the processor 304, at a selected sample rate (for example, 4 kHz) and at a selected resolution (for example, 12 bits). Signals from the accelerometer 302a may be collected at a selected accelerometer sampling rate (for example, 1 kHz) and at a selected resolution, which may also be 12 bits of resolution. It is noted that one or more of the sensors may be implemented in modules that pre-process the electrical signals that communicate the sensor modality. For example, the accelerometer 302a may include ADC functionality and a communication interface with the processor 304. In an example implementation, the communication interface is a serial bus interface, such as I2C or SPI. Any suitable communication interface may be used depending on the specific requirements of the implementation.

It is noted that examples of the wearable patch 300 may be deployed to detect signals from varying sensory modalities in which signal strength and noise may affect the capture of the signals to varying degrees. It would be advantageous to add gain varying capabilities and different types of filtering to obtain a desirable sensitivity and accuracy. The gain of the front end for each analog channel may be independently programmable via a configuration block, for example, by selecting among resistors, for example, on several output ports. Gains of 1×, 5× and 20× may be pre-installed on switchable input pins. A digital filter may be implemented to block 60 Hz AC frequency noise from the microphone, piezo and accelerometer channels. Data may be captured into RAM in a buffer of a suitable size. Once a buffer is filled, data capture may continue in the second buffer, and data in the first buffer may be filtered, delta compressed, and stored in memory 322 without interrupting data capture. In an example implementation, the memory 322 may accommodate the storage of sensor data captured before a connection via the communications interface is available.

Data reads may include a timestamp, which may be provided by the processor 304 when processing the sensor data for communication.

Sensor Suite Selection

Several classes or types of sensors may be used in the sensor assembly and selected based on their ability to transduce clinically relevant data. Sensor suites may be configured in which the sensors are selected for their relevance to specific applications. The wearable patch 300 in FIG. 3A includes the following sensors to perform the indicated functions:

1. Microphone 302b—the microphone 302b may be used to measure the acoustic signature of blood flow through the fistula in an example implementation in one example application (e.g. monitoring of an AV fistula). This is consistent with current clinical practices and most closely resembles the use of a stethoscope to assess the health of an AV fistula. Microphone 302b may be a MEMS microphones, which typically have silicon nitride or other thin-film membranes, and which are sensed capacitively. Alternatively, the microphone 302b may be made of a piezoelectric material, such as for example, polyvinylidene fluoride (PVDF) or lead zirconate titanate (PZT). The PVDF material has an acoustic impedance very similar to biological tissue. A PVDF sensor that is conformally attached to the skin may allow for elimination of impedance matching components that add to the bulk of traditional stethoscopes. The PVDF sensor may be attached directly on the skin in the area of the fistula using a biocompatible adhesive with suitable acoustic impedance. An example of an adhesive would be a hydrogel adhesive, which typically has comparable acoustic impedance to biological tissue and PVDF.

2. Accelerometer 302a—the accelerometer 302a allows for detection of the fistula health and may operate as an inclinometer (i.e. motion sensing).

3. Temperature sensor 302d and 302e are temperature sensors that are placed at different locations on the user's arm and measured differentially. The temperature sensors 302d and 302e may be used to infer blood flow in the fistula.

4. Piezoelectric sensor 302c may be used as a strain gauge and may take the form of a stretched piezoelectric diaphragm or a piezoelectric sensor in compression driven by a diaphragm and configured to produce an AC acoustic signal.

Again, other sensors can be used in place of the sensors shown in FIG. 3A or different sensors may be added (e.g. optical sensors such as PPG sensors) to enhance the diagnostic capabilities of the wearable patch as needed in specific implementations.

Power Management/Shelf Mode

The wearable patch 300 includes a shelf mode wakeup sensor 310 (described above as the shelf sensor 210 in FIG. 2), which may be implemented as shown in FIG. 3A using a normally closed magnetic reed switch connected to a battery 312. The shelf mode wakeup sensor 310 switches power from the battery 312 to the rest of the system to an off state when the shelf mode wakeup sensor 310 is in an open state. The wearable patch 300 may be stored prior to deployment in packaging that includes a magnetic adhesive backing liner 314 applied to adhesive on the wearable patch 300. When the magnetic adhesive backing liner 314 is attached to the wearable patch 300, the shelf mode wakeup switch 310 is kept in an open state by the magnetic field from the adhesive backing liner 314 thereby keeping battery power disconnected from the other components. When the adhesive backing liner 314 is removed during deployment of the wearable patch 300 on the patient's body, the shelf mode wakeup switch 314 closes, thereby restoring power to the remaining components on the wearable patch 300. Once power is present, the wearable patch microcontroller 304 actuates a shelf mode lockout switch 316, which prevents the shelf mode wakeup switch 314 from returning the device to shelf mode without an explicit command from the microcontroller 304 to unlock the shelf mode lockout switch 316.

Figure 3B:
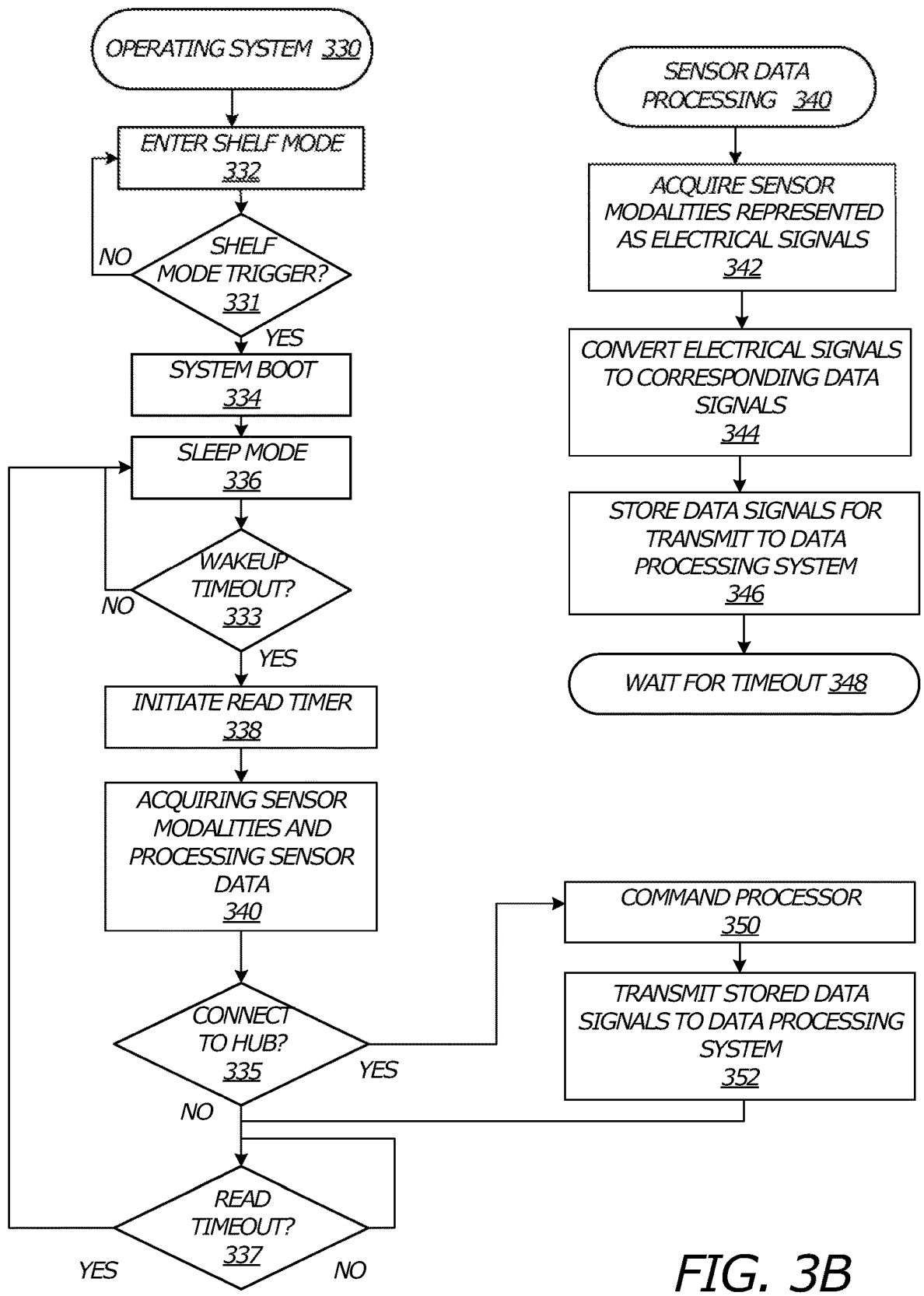
FIG. 3B is a flow diagram illustrating operation of an example operating system for the wearable patch of FIG. 3A.

The wearable patch 300 in FIG. 3B includes a power switch 320, which may be implemented using a nanoboost converter with integrated load switch. In the illustrated example, the power switch 320 applies battery voltage to two 3.0 V (for example) buses:

1. Vcc, which is used to power the processor 304, and
2. Vsec, which is used to power the sensors and a memory module 322. The power switch 320 may be configured to consume power at nA levels in a quiescent (low power/low demand) state.

The wearable patch 300 also includes a wakeup sensor, which may be implemented using a real-time clock plus switch (RTC/switch) 318 in an example implementation. The RTC/switch 318 may be configured to maintain a timestamp and is configured to power up the processor 304 on a time schedule. The processor 304 provides power to a secondary bus as needed by the wearable patch 300 application via a digital I/O output from the processor 304 configured to drive the power switch 320. Before entering a sleep mode, the processor 304 deactivates the secondary bus.

Between data reads and transmits, the processor 304 may enter a deep sleep mode with the watchdog timer (wakeup sensor 318) set to wake it on schedule. The boost converter load switch (power switch 320) may be used to shut off all power to the memory 322, the accelerometer 302a and the microphone 302b.

Operation of the Wearable Patch—Modes of Operation

FIG. 3B is a flowchart of a wearable device operating system 330 illustrating operation of an example implementation of a wearable patch, such as the example wearable patch 300 described above with reference to FIG. 3A. The flowchart of the wearable device operating system 330 in FIG. 3B may be implemented using a state machine or any other suitable processing scheme.

The flowchart of the wearable device operating system 330 in FIG. 3B begins operation in a shelf mode at step 332. In the shelf mode at step 332, the wearable patch is not provided with power to its electronic components, such as the processor, etc. The shelf mode allows for the wearable patch to be shipped and put "on a shelf" for long-term storage before deployment without the electronic devices consuming any power, or at least a substantial amount of power. In the shelf mode, the wearable patch is in a powered off state until power is connected to the wearable patch by actuating a shelf mode wake up sensor 310 (shelf sensor 210 in FIG. 2). Decision block 331 determines if the shelf mode has been triggered. In an example implementation, the shelf mode may be triggered when the shelf mode wakeup sensor 310 is implemented using a magnetic switch, and a magnetic field generated by the product packaging is removed when the wearable patch is removed from the product packaging. The product packaging providing the magnetic field may be a product container such as an envelope, or an adhesive backing liner. Various implementations of the shelf sensor 210 (in FIG. 2) are described above with reference to FIG. 2 and may all be used in decision block 331.

If the shelf mode is triggered, power is applied to the electronic devices on the wearable patch. The processor performs a system boot at step 334, which may involve the initialization of parameters, registers, memory locations, etc. as well as of the sensors in the sensor assembly. Once the system boot at step 334 is complete or nearly complete, the processor initiates a timer, or a watchdog timer, for example. The wearable patch operating system may then enter a sleep mode at step 336. In the sleep mode, the wearable patch may be in a low power state thereby conserving power while the wearable patch is not performing any functions other than the watchdog count. Decision block 333 represents the wakeup count or the count down (or count up) of the watchdog timer. At predetermined time intervals based on the watchdog time, the wearable patch powers up and performs signal acquisition and processing functions.

In an example implementation, the wearable patch may be awakened by either the watchdog timer or the shelf mode wakeup sensor. Examples of the wearable patch may include mechanisms that allow a user to manually trigger the wearable patch to exit the deep sleep mode. Manual exit from the deep sleep mode may be implemented to allow for a data processing system to connect to the wearable patch via the communication interface 206 (in FIG. 2) to receive commands to, for example, perform a manual sensor acquisition function, or to transmit sensor data to the data processing system, or other functions that may be desired in an example implementation. A command processor function is described below.

When the wakeup timeout occurs (the "YES" path from the decision block 333), the wearable patch is in a wake state. Power is applied to the any active sensors, to any amplifiers, the processor, and other components needed to perform the functions involved in the wake state. A read timer may be started at step 338 to provide a time window during which the wearable patch performs acquisition functions, sensor data processing functions, and transmission of sensor data to the data processing system, as well as any other functions that may be desired in a specific implementation.

Once the read timer is initiated, the wearable patch operating system begins the function of acquiring sensor modalities and processing the sensor data obtained from the sensor modalities at step 340. Operation of an example method for acquiring sensor modalities and processing the sensor data is illustrated in a flowchart for sensor data processing in step 340 in FIG. 3B. The functions of step 340 may be performed in parallel with other functions that may be performed by the wearable patch operating system.

At step 342, sensor modalities represented as electrical signals are acquired from the sensors. At step 344, the electrical signals may be converted to sensor data signals. The conversion performed at step 344 may be performed by the processor using, for example, an ADC function. For example, the processor may receive analog audio input signals from the microphone 302b (in FIG. 3a) and convert the analog signals to digital samples. The conversion of electrical signals to sensor data signals may also be performed at least partially by the sensor component. For example, a sensor such as the accelerometer, temperature sensor, or any other modular sensor component, for example, may be provided with ADC functions as well as an appropriate bus interface that permits digital communication with the processor. The processor may then perform any signal conditioning functions, such as filtering or other signal processing functions before storing the sensor data signals for later transmission to the data processing system at step 346.

At step 348, the sensor data processing step 340 may be complete and the operating system may be performing other functions or waiting for the read timer to timeout. One of these functions, at step 350 is to connect to the data processing system. In example implementations, the connection to the data processing system is a wireless connection using for example, Bluetooth BLE™ or another suitable protocol. The connection to the data processing system may permit the wearable patch operating system to execute a command processor at step 352 in which the data processing system transmits commands to the wearable patch to perform. Such commands may be a manually initiated sensor acquisition function or other functions related to diagnostics, system configuration, manually initiated data transmission of the contents of the memory, manually changing the mode or state of the wearable patch, or other functions as desired in a specific implementation. During the connection to the data processing system, the stored sensor data is transmitted at step 354.

It is noted that the duty cycle involved for the applications that may be performed by the wearable patch are sufficiently short so that the operation time of the wearable patch is far shorter than the sleep time (at low power). In some example implementations, the sleep time may be as long as one to three hours while the operation time may be as short as five seconds.

It is also noted that the flowchart depicts steps to be performed by the wearable patch operating system generally in the order in which they'd be performed in an example implementation. Some steps or functions may be performed in parallel or in a multi-tasking environment depending on what is desired for the specific implementation. For example, in some implementations, the sensor modality acquisition step 340 and connection to the data processing system step 350 need not be performed in any specific order, or in every read timer cycle. For example, the connection to the data processing system step 350 may be performed at each read timer cycle, while the sensor modality acquisition step 340 may be performed once every two, three, or other number of read timer cycles. That is, a short read timer cycle may be defined for the connection to the data processing system step 350 and a longer cycle may be defined for the sensor modality acquisition step 340. In addition, during each connection to the data processing system step 350, the wearable patch may be programmed to communicate advertising messages to the data processing system for display on a monitor or other suitable display output device and to enter into the command processor step 352 to operate under the control of the data processing system.

Decision block 337 determines if the read timer has timed out. If the read timer has timed out, control returns to the sleep mode at step 336 (the "YES" path of decision block 337). Otherwise, the system waits for the read timer to timeout (the "NO" path of decision block 337).

FIG. 3C is a block diagram of the processor 304 that may be used in the example of the wearable patch 300 shown in FIG. 3A. The processor 304 in FIG. 3C includes a microcontroller function 350, an ADC function 352, an analog signal conditioning function 354 to interface with the sensors 302, a BLE interface 356, a connection to an oscillator 358, a FLASH/RAM memory 360, and a connection to a battery 312, which may include a connection to a charger 370 with an interface 372 to a charger source.

The microcontroller 350 may be of a type that may be programmed to perform, or may include signal processing functions. In some implementations, the microcontroller 350 may be programmed to collect raw data for further processing by a hub element, or by a remote data processing system. The processor 304 in FIG. 3C illustrates one example of the types of interfaces and features that may be included to perform processing functions on the wearable patch 300. Other processors 304 may include more or fewer features and functions. The processor 304 in FIG. 3C uses a BLE standard communications interface, but other suitable communications interfaces may be used. Some functions of the analog signal conditioning functions 354 are described above with reference to FIG. 3A. Other analog signal conditioning functions may be on other selected processors, which may be selected according to the type of sensors 302 included in the sensor assembly.

In an example implementation, the processor 304 may be implemented using a Cypress PSOC BLE module, which is based on a Cortex M0 ARM core (MCU 350), contains 256 MB FLASH, 32 KB RAM and supports BLE 4.2. As emphasized above, a specific processing element to use as the processor 304 will depend on the specific requirements of specific implementations.

Figure 3D:
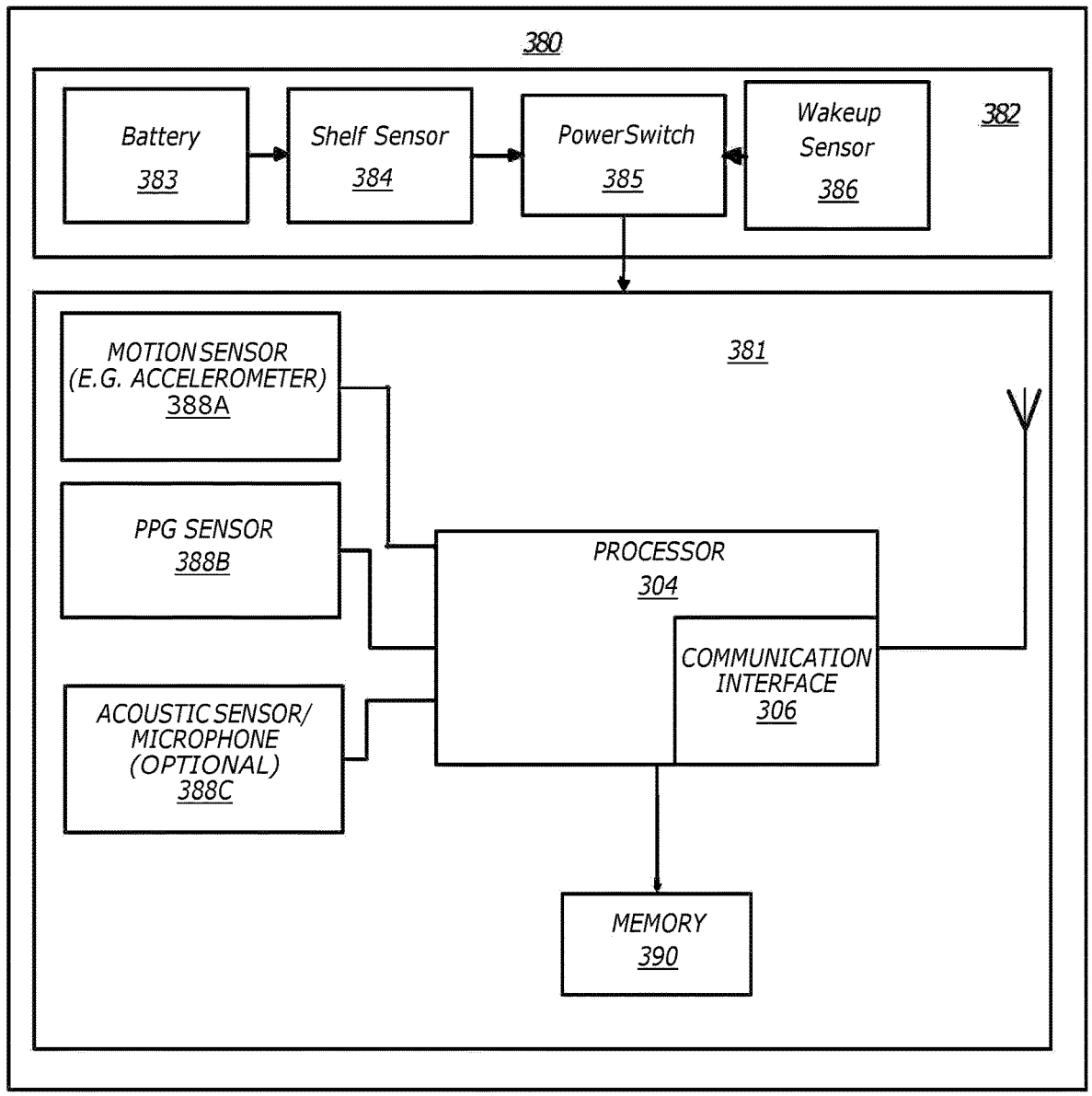
FIG. 3D is a block diagram of an example implementation of another wearable patch.

FIG. 3D is a block diagram of an example implementation of another wearable patch 380. The wearable patch 380 in FIG. 3D is illustrated as an example of the wearable patch 200 in FIG. 2. The wearable patch 380 includes a power module 382, which includes a battery 383, a shelf sensor 384, a power switch 385, and a wakeup sensor 386. The power module 382 may be implemented as described for the power module 203 in FIG. 2. The battery 383, the shelf sensor 384, the power switch 385 and the wakeup sensor 386 may be implemented as described for their corresponding components with reference to both FIG. 2 and FIG. 3A. Similarly, the wearable patch 380 in FIG. 3D includes a processor 304, a communication interface 306, and memory 390, which may operate as described for the processor 304, the communication interface 306, and memory 322 in FIG. 3A as well as the corresponding components described more generally with reference to FIG. 2.

The wearable patch 380 in FIG. 3D includes a sensor assembly 388 that includes a motion sensor 388A (which may be implemented as an accelerometer), a Photoplethysmogram (PPG) sensor 388B, and an acoustic sensor 388C (which may be implemented using a microphone or a piezo sensor as described above with reference to FIGS. 2 and 3A). The PPG sensor 388B is used to obtain a plethysmogram (PPG), which is a volumetric measurement of an organ, using an optical interface. The PPG sensor 388B includes one or more light sources, which direct light into the skin on which the wearable patch 380 is mounted, and a light sensor, which detects light reflected from the tissue that receives the light. The PPG sensor 388B is similar to a pulse oximeter, which measures changes in light absorption by the skin. In this manner, the PPG sensor 388B monitors multiple parameters related to the blood content below the skin on which the wearable patch 380 is mounted. When an example implementation of the patch 380 in FIG. 3 is applied over an area of skin with an arteriovenous access directly below the patch 380, these parameters include but are not limited to: volumetric blood flow rate, hematocrit, oxygen saturation, change in blood volume, and total blood volume.

Each cardiac cycle of the heart pumps blood to the periphery and is detectable as a pressure pulse. The changes in volume caused by the pressure pulses is detected by illuminating the skin with light from, for example, an LED on the PPG sensor 388B and then measuring the amount of light reflected to a photodiode on the PPG sensor 388B. The PPG obtained from the PPG sensor 388B includes peaks representing each cardiac cycle. Because blood flow to the skin can be modulated by multiple other physiological systems, the PPG can also be used to monitor breathing, hypovolemia, and other circulatory conditions, such as for example a level of stenosis of a vessel.

In some example implementations, the motion sensor 388A, the PPG sensor 388B and the acoustic sensor 388C can be utilized in conjunction with one another to provide monitoring of additional physiological parameters that would not be measurable by the motion sensor 388A, the PPG sensor 388B and the acoustic sensor 388C individually. For example, if the wearable patch is worn over an area of tissue which has an arteriovenous access directly below it, the motion sensor 388A, if implemented as a 3-axis accelerometer, can also be utilized in conjunction with the PPG sensor 388B to monitor and calculate a patient's blood pressure. PPG sensors have been utilized to estimate blood pressure, however, many of them suffer from inaccuracy due to the lack of a reliable mechanical measure of vessel compliance. A 3-axis accelerometer is able to measure vessel compliance and acceleration directly and simultaneously with the PPG sensor because it will be able to measure acceleration in the x, y and z directions separately. Thus, the combination of a 3-axis accelerometer with a PPG offers an accurate assessment of both the blood volume and the acceleration of the vessel wall caused by blood flow. This yields the necessary components for calculating a blood pressure since the multiplication of the z-axis acceleration (based on measurements using the motion sensor 388A) and mass of blood (calculated from the volume measured by the PPG sensor 388B) will equal the force applied by the blood to the vessel wall. Once this is known, dividing this value by the area of the vessel wall which is measured by the PPG sensor 388B will yield a blood pressure value.

The values measured by the individual sensors and through combinations of readings from the individual sensors may allow for more complete management of patient's health. The wearable patch 380 from FIG. 3D, when applied to a patient with an arteriovenous access undergoing hemodialysis could be utilized to provide complete management of the patient's access and cardiovascular health. The combination of measurements described in the above example implementations (blood volume, volumetric flow rate, hematocrit, oxygen saturation, vessel stenosis, and blood pressure) can be utilized to manage a patient's fluid status, dry weight, and dialysis dose.

In some example implementations the motion sensor 388A, the PPG sensor 388B, and the acoustic 388C can be used in conjunction with one another to enhance accuracy of measurement. For example, the motion sensor 388A may be used to identify any motion artifacts in the output of the PPG sensor 388B. The acoustic sensor 388C may be used to obtain acoustic information that would identify turbulent flow that would affect the signal obtained by the PPG sensor.

The wearable patch 380 is described to provide an example of another sensor assembly. In a sense, all sensors that may be added to a sensor assembly are optional and are selected for inclusion in a sensor assembly based on the application for which the wearable patch is to be used and the desired functional and performance characteristics for the specific wearable patch.

Figure 4A:
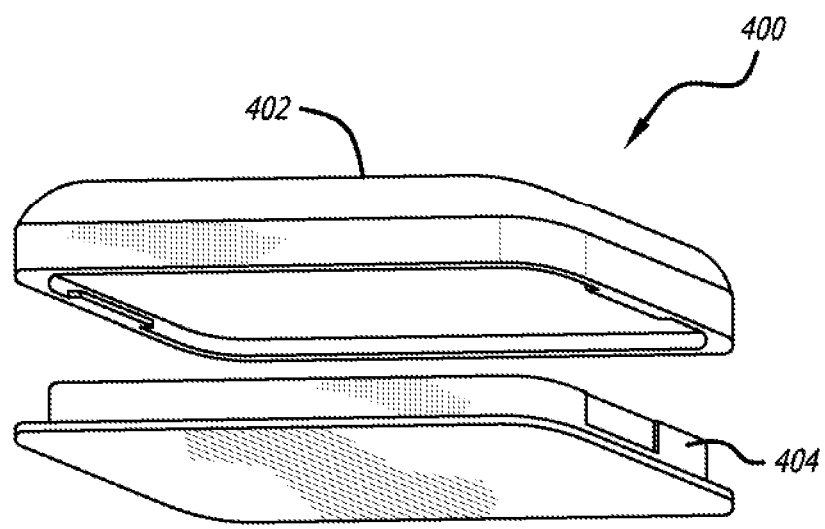
FIG. 4A is a perspective bottom view of an example of a wearable patch.
Figure 4B:
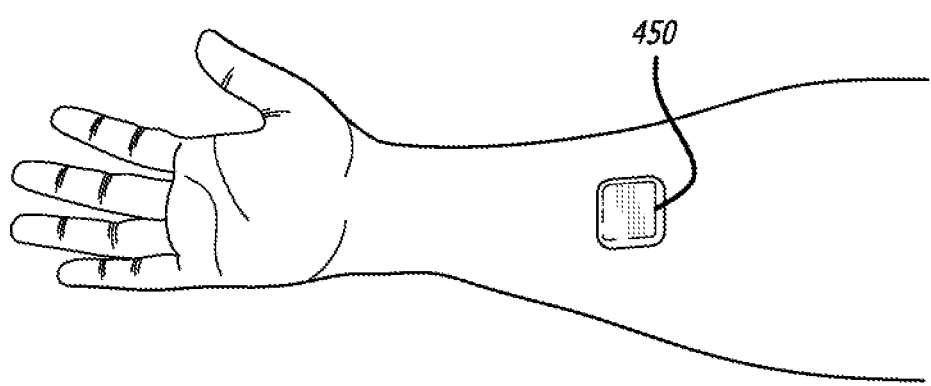
FIG. 4B is a top view of an example of a wearable patch.

FIG. 4A is a perspective bottom view of an example of a wearable patch 400. FIG. 4B is a top view of an example of a wearable patch 450 attached to a patient's arm. The wearable patch 400 or 450 in FIGS. 4A and 4B is intended to be worn over a fistula and configured to communicate to a nearby sensor data processing system, which may include a local hub for forwarding data to a backend, or remote sensor data processor. In the examples described above, the wearable patch 400 or 450 communicates using a BLE interface, although other suitable interfaces may be used.

The wearable patch may be formed with 1 or 2 parts. FIG. 4A depicts an example wearable patch 400 formed in 2 parts, a first part 402 and a second part 404.

If the wearable patch is in 1 part, then the adhesive may be a replaceable component and the device may be configured as a patch substrate to house electronics components, while still enabling adequate coupling of the sensor(s) to the skin for conformal attachment.

If the wearable patch is formed in 2 parts, the part connected to the skin would be the patch substrate implemented as a flexible adhesive layer supporting the sensor assembly and optionally any of the other electronic components of the wearable patch. Optionally, the patch substrate supports the sensor assembly and the second part includes encapsulated electronics (i.e. the processor, signal conversion, and communications interface). The mechanical features on both parts that connect the two parts may also include electrical connectors that would enable communication between the sensor assembly and the electronics (processor, signal conversion, communications interface, etc.). The mechanical features of the sensor/adhesive part would be flexible to enable conformal attachment of the sensor assembly and adhesive to the skin, while still allowing for secure mating with the rigid, encapsulated electronics. The overall size of the wearable patch, including the height, may be an important factor that affects comfort. The wearable patch may be powered by a battery, which would likely be the largest component.

Method for Monitoring a Patient

Figure 5:
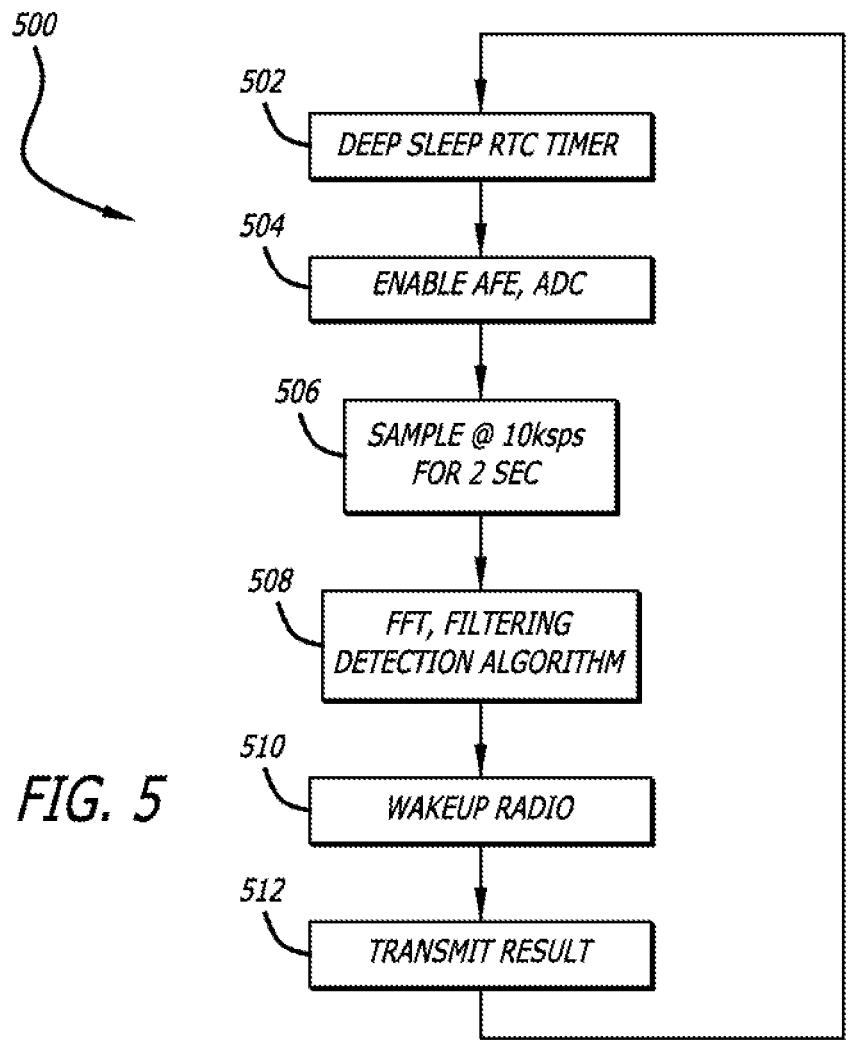
FIG. 5 is a flowchart illustrating operation of a method for monitoring subcutaneous processes in a patient wearing a wearable patch.
Figure 6:
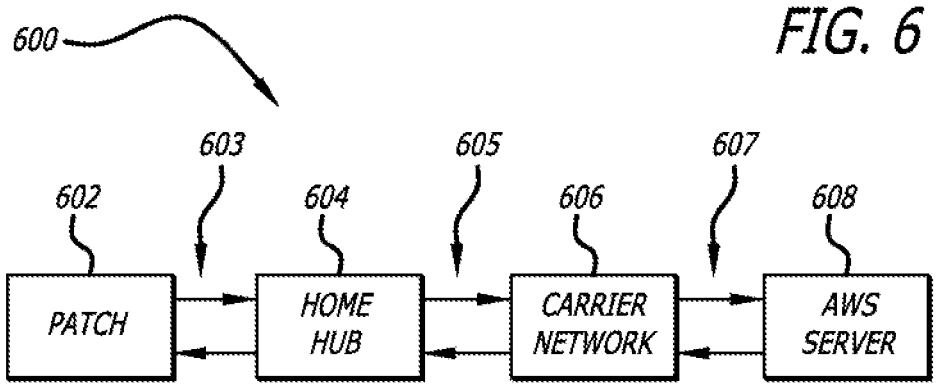
FIG. 6 is a block diagram of an example system for monitoring a patient wearing a wearable patch.

Determining either a thrombosis alert or level of stenosis requires a few steps of signal processing to get data from the sensor digitized and analyzed. The above descriptions with reference to FIGS. 2 and 3A-3D of example implementations of a wearable patch includes a description of how data may be extracted from the sensors and processed for transmission to a data processing system. FIGS. 5 and 6 illustrate example implementations of the signal conversion functions of the wearable patch and how the wearable patch may communicate sensor data to a data processing system.

FIG. 5 is a flowchart illustrating operation of an example of a method 500 for obtaining and processing data from a sensor assembly. The method in FIG. 5 includes signal conversion functions that may be incorporated in example implementations of the operating system and sensor data acquisition methods described above with reference to FIG. 3B.

The method 500 in FIG. 5 may be performed using any suitable sensor assembly with access to signal conversion functions, which may be implemented using modular sensors with signal conversion functions included (e.g. the accelerometer 302a described above with reference to FIG. 3A), a processor that uses a real time clock timer, an ADC function and signal processing capabilities including for example, Fast Fourier Transform (FFT) tools, digital filtering functions, and signal detection algorithms.

The method 500 illustrated in FIG. 5 begins at step 502 in which the processor is in a sleep mode, and a real-time clock (RTC) timer is set to wake the processor periodically. An example of this process is described above with reference to FIG. 3B. The processor enables the analog front end (AFE) and the ADC function at step 504. The AFE refers to an interface to sensors in the sensor assembly that communicate analog signals to the processor. When enabled, the sensors begin to receive sensory modalities. The sensors convert the sensory modalities to electrical signals, which are then sampled by either the ADC function on the processor at, for example, 4 k samples/sec for 5 seconds, or by a signal conversion function incorporated on the sensor component, as indicated in step 506. Digital samples generated by signal conversion functions on the sensors are communicated to the processor on a bus, such as a serial bus (e.g. I2C bus, SPI bus, etc.) or a parallel bus.

The digital samples representing the electrical signals from the sensors may be processed using digital signal processing functions, such as for example, Fast Fourier Transform (FFT) or a filtering detection algorithm or other suitable functions, as deemed useful for each signal, as indicated in step 508. At step 510, the communications interface is awakened for transmission of the sensor data. The processor generates the sensor data signal from the digital signal processing functions and formats the sensor data according to a selected communication protocol. The sensor data signal is then transmitted at step 512 via the communication interface.

The wearable patch may transmit results wirelessly after the sensing operation. In an example implementation, Bluetooth Smart™ is a low power radio technology that may be used to communicate to a relay or local hub. The local hub transfers the results to a backend system, such as the remote sensor data processor in the network. Storage and further processing of the sensor data may be performed on the remote sensor data processor, which may be implemented on a remote server. A front-end interface may be configured to communicate alerts to a clinician.

FIG. 6 is a block diagram of an example system architecture for a system for monitoring a patient wearing a wearable patch. The system in FIG. 6 includes a patch 602 connected to a local hub 604 via a BLE connection 603. Any other suitable local communication protocol may be used as well as discussed above. The local hub 604 is connected to a carrier network 606 using a cellular link 605. The carrier network 606 in the illustrated example is a cellular data system, but may be any other suitable network infrastructure, such as the Internet where connection to the Internet is achieved using a WiFi system, a hardwired Ethernet connection, or any other infrastructure that may be used for communicating remotely. In the example in FIG. 6, the carrier network 606 connects the home hub 604 over the Internet to an Amazon Web Service (AWS). The AWS is a cloud-based computing service. Other cloud-based services are available from Microsoft, Oracle and other, and may be used as well.

It is noted that some example implementations may not include the local hub 604. The patch 602 may be implemented with the capability to communicate sensor data directly over the Internet to a cloud service, for example, or other systems for processing the sensor data.

Determining a Level of Stenosis

Examples of a wearable patch may be used as part of a system to monitor and alert for thrombosis development or clinically actionable levels of stenosis in a vessel such as an AV fistula or graft. Alerts may be triggered by the system and lead to a clinical pathway whereby the patient is examined by a care provider and put through a diagnostic pathway including but not limited to duplex ultrasound, fistulogram and/or arteriograms. The results of the diagnostic studies combined with the monitoring result from the patch could lead to a corrective intervention such as a drug prescription, thrombectomy or angioplasty to clear the blocked fistula. In some cases, the diagnostic process may lead to another surgery for the patient to place a new fistula, HERO graft or central venous catheter.

The wearable patch may be worn to enable an AV fistula or Graft to reach maturation, or to help lengthen the lifetime of an AV fistula or graft. The wearable patch may be worn by the patient and communicate data and alerts multiple times in a given day. The patient may remove the electronics from the patch (if the device is constructed as a two-part patch) periodically, or replace disposable components of the patch (e.g. adhesive) depending upon the specific protocol.

During a clinician or home visit, the wearable patch may be removed and charged to replenish the battery. In the case of an AV fistula patient, the battery-charging may be performed during the dialysis session.

Standard clinical protocols typically require a check of the patency of an AV fistula or graft during a physical examination on routine visits to a clinician. The clinician can "feel the thrill" of flow through the access, and also listen for the bruit using a conventional stethoscope. A change of the character of the bruit to a higher pitch can indicate the presence of stenosis or thrombosis. Various methods may be used to quantify the stenosis using the digital output of a stethoscope, or to determine if a thrombosis has formed. One example is to use a break frequency to estimate the internal diameter of the carotid artery in patients. This technique is referred to as phonoangiography. The break frequency may be determined a number of ways. A frequency power spectrum may be calculated for an acoustic sensor output and used to identify the highest frequency after which the power drops off significantly. A higher break frequency is correlated with a narrower vessel, and thus a higher level of stenosis. Break frequency values typically fall between 10 and 1000 hz., where a value closer to 1000 would indicate a significant degree of stenosis (>50%). In AV fistulas, metrics such as the break frequency may be utilized to determine either thrombosis or stenosis.

A key difference may exist for the utilization of break frequency for AV fistulas as opposed to a carotid artery. In the carotid artery, a bruit is indicative of unhealthy flow, while in the AV fistula a bruit is indicative of healthy flow. Thus, the correlation in AV fistula may be reversed from those found in the carotid artery, with a lower level of bruit (i.e. a lower break frequency) indicating a higher degree of stenosis or potentially even thrombosis. Additional analytic methods are possible for AV fistulas/grafts such as using autoregression to calculate the power spectral density. The advantage of such a method is that it may be more effective at quantifying stenosis levels at lower flow rates. A combination of different analytical methods would likely be beneficial to determine the level of stenosis or if a potential thrombosis has occurred in an AV access.

The wearable stethoscope patch would enable this analysis by detecting these signals and automatically transmitting them for analysis over the course of a patient's life and treatment.

EXAMPLE IMPLEMENTATIONS LIST

The disclosure presented herein may be considered in view of the following example embodiments:

Example 1: A wearable patch for sensing information relating to subcutaneous processes in a patient, the wearable patch comprising: a patch substrate configured to attach to a body part of a patient; a sensor assembly mounted on the patch substrate, the sensor assembly comprising a plurality of sensors configured to detect a corresponding plurality of sensory modalities and generate electrical signals representing the sensory modalities; a signal converter configured to receive the electrical signals from the plurality of sensors and to convert the signals to sensor data signals comprising a data representation of at least one of the electrical signals; a communications interface configured to communicate the sensor data signals to a sensor data processing system.

Example 2: The wearable patch of Example 1 where the sensor assembly includes any of an acoustic sensor, an accelerometer, a temperature sensor, a strain gauge, an optical sensor, a photoplethysmogram (PPG) sensor, a moisture sensor, a conductivity sensor, a pressure sensor, or a chemical sensor.

Example 3: The wearable patch of any of Examples 1 or 2 where the sensor assembly includes an ultrasonic transducer and an ultrasonic sensor.

Example 4: The wearable patch of any of Examples 1 to 3 where the sensor assembly includes two temperature sensors configured to provide a differential temperature measurement.

Example 5: The wearable patch of any of Examples 1 to 4 where the sensor assembly includes an acoustic sensor and an accelerometer.

Example 6: The wearable patch of Example 5 where the acoustic sensor is a piezoelectric device.

Example 7: The wearable patch of Example 6 where the piezoelectric device is made of a material selected from any of polyvinylidene fluoride, lead zirconate, a composite including either PVDF or PZT materials.

Example 8: The wearable patch of Example 5 where the acoustic sensor is a microphone.

Example 9: The wearable patch of any of Examples 1 to 8 where the communication interface includes a wireless transmitter to transmit the sensor data signals to the sensor data processing system.

Example 10: The wearable patch of Example 9 where the wireless transmitter communicates radio frequency (RF) signals.

Example 11: The wearable patch of Example 10 where the radio frequency signals are communicated using a near field communication protocol.

Example 12: The wearable patch of Example 10 where the radio frequency signals are communicated using the Bluetooth Low Energy (BLE) protocol.

Example 13: The wearable patch of Example 10 where the wireless transmitter communicates using a cellular communications system.

Example 14: The wearable patch of Example 10 where the wireless transmitter communicates using a WiFi system or a near field magnetic communication system.

Example 15: The wearable patch of any of Examples 1 to 14 where the sensor assembly, signal converter, or communications interface operate using a power source on the wearable device, and the wearable patch is configured to operate in a shelf mode for low power operation of the sensor assembly, signal converter, or communications interface.

Example 16: The wearable patch of Example 15 where when the wearable patch enters the shelf mode, power is disconnected to the sensor assembly, the signal converter, and the communications interface.

Example 17: The wearable patch of Example 15 where when the wearable patch enters the shelf mode, the sensor assembly, signal converter, and communications interface operate at a reduced power.

Example 18: The wearable patch of Example 15 further comprising a shelf mode wakeup switch configured to maintain the wearable patch in the shelf mode until the shelf mode wakeup switch changes state triggered by deployment of the wearable device.

Example 19: The wearable patch of Example 18 where the shelf mode wakeup switch is any one of the following: a magnetic switch, a magnetic sensor, an optical sensor, a motion, acceleration or tilt sensor, a temperature sensor, a capacitive proximity sensor, and a mechanical switch.

Example 20: The wearable patch of Example 18 where the shelf mode wakeup sensor is configured to switch states to trigger an exit of the shelf mode by removal of product packaging when the wearable patch is being deployed for attachment to the patient.

Example 21: The wearable patch of Example 20 where the wearable patch includes an applicator component configured to generate a magnetic field, and the shelf mode wakeup sensor is a magnetic switch maintained in a first state corresponding to the shelf mode when in proximity to the applicator component sufficient to detect the magnetic field, where the magnetic switch is triggered to exit the shelf mode by separation of the wearable patch from the applicator component during deployment of the wearable patch for attachment to the patient so that the magnetic switch is not in sufficient proximity to the magnetic field to detect the magnetic field.

Example 22: The wearable patch of Example 21 where the applicator component is an adhesive backing liner having a magnetic component.

Example 23: The wearable patch of Example 20 where the shelf mode wakeup sensor is an optical sensor precluded from sensing light by the product packaging, where the optical sensor maintains the wearable patch in the shelf mode when precluded from sensing light and to exit the shelf mode and permit power to the wearable patch when able to sense light when separated from the product packaging.

Example 24: The wearable patch of Example 23 where the product packaging is a product container package sufficiently opaque to preclude the optical sensor from detecting light.

Example 25: The wearable patch of Example 23 where the product packaging is an opaque adhesive backing liner abutting the optical sensor while packaged to preclude the optical sensor from detecting light.

Example 26: A system for monitoring a patient comprising: a wearable patch configured to attach to a body part of a patient, the wearable patch comprising: a sensor assembly comprising a plurality of sensors configured to detect a corresponding plurality of sensory modalities and generate electrical signals representing the sensory modalities; a signal converter configured to receive the electrical signals from the plurality of sensors and to convert the signals to sensor data signals comprising a data representation of at least one of the electrical signals; and a communications interface configured to communicate the sensor data signals; and a sensor data processing system configured to receive sensor data signals from the wearable patch.

Example 27: The system of Example 26 where the sensor data processing system comprises: a local hub configured to wirelessly receive the sensor data signals from the wearable patch using a first protocol, and to transmit the sensor data signals using a second protocol; a remote sensor data processor configured to receive the sensor data signals using the second protocol and to process the sensor data signals to monitor and alert for thrombosis development or clinically actionable levels of stenosis in a vessel.

Example 28: The system of Example 27 where: the first protocol is a short range wireless communication protocol.

Example 29: The system of Example 28 where the short range wireless communication protocol is a wireless protocol including the Bluetooth™ protocol, a near field communication protocol, a WiFi protocol, or a near field magnetic protocol.

Example 30: The system of Example 27 where: the second protocol is long range wireless protocol including any of a cellular protocol or an Internet protocol.

Example 31: The system of Example 26 the sensor data processing system includes a processor and a storage medium storing computer-executable instructions that when executed are operable to: perform phonoangiography using a break frequency to estimate an internal diameter of a carotid artery for the patient.

Example 32: The system of Example 26 where the storage medium stores computer-executable instructions that when executed are operable to: determine the break frequency by calculating a frequency power spectrum for a sound measurement and identifying a highest frequency after which a power level drops significantly.

Example 33: A method for monitoring subcutaneous processes in a patient comprising: sensing a plurality of sensory modalities using a sensor assembly comprising a plurality of sensors mounted on a wearable patch, where the sensory modalities are received as electrical signals representing the sensory modalities; converting the electrical signals to a plurality of corresponding sensor data signals; and transmitting the sensor data signals to a sensor data processing system.

Example 34: The method of Example 33 where the step of sensing the plurality of sensory modalities includes any of: sensing sound using an acoustic sensor; sensing movement or orientation of a patient body part using an accelerometer; sensing temperature using a temperature sensor; sensing a stretch or compression of the wearable patch using a strain gauge; sensing electromagnetic signals using an optical sensor; sensing moisture using a moisture sensor sensing conductivity using a conductivity sensor; sensing pressure using a pressure sensor; sensing oxygenation or flow volume using an optical sensor or a photoplethysmograph; and sensing a chemical using a chemical sensor Example 35: The method of any of Examples 33 and 34 where the step of sensing the plurality of sensory modalities includes sensing a differential measurement of skin temperature from two temperature sensors.

Example 36: The method of any of Examples 33 to 35 where the step of transmitting the sensor data signals to the sensor data processing system comprises: transmitting the sensor data signals to a local hub in substantially close proximity to the wearable patch, where the local hub transmits the sensor data signal to a remote sensor data processor for processing of the sensor data signals.

Example 37: The method of any of Examples 33 to 36 where the wearable patch includes a power source, a processor, components for performing the steps of the method, and a shelf mode wakeup switch, the method further comprising: entering a shelf mode where the power source is not connected to the sensor assembly, the processor, or the components for performing the steps of the method when the shelf mode wakeup switch in a first state; and exiting the shelf mode to connect the power source to the sensor assembly, the processor, and components for performing the steps of the method when the shelf mode wakeup switch switches to a second state.

Example 38: The method of Example 37 where: in the step of entering the shelf mode, the wearable patch is enclosed in product packaging prior to deployment configured to interact with the shelf mode wakeup sensor to maintain the shelf mode wakeup sensor in the first state; and in the step of exiting the shelf mode, removal of the wearable patch from the product packaging triggers the shelf mode wakeup sensor to switch to the second state.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the processor. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), application specific integrated circuits (ASICs), field-programmable gate array (FPGAs), etc. Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" or "in electrical communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A wearable device for sensing information relating to subcutaneous processes in a patient, the wearable device comprising:
    an adhesive patch configured to attach to a body part of the patient at a location that provides subcutaneous access to a vessel being an artery, a vein, or an arteriovenous (AV) access;
    a sensor assembly mounted on the adhesive patch, the sensor assembly comprises one or more sensors and each sensor of the one or more sensors is configured to generate one or more electrical signals corresponding to a sensory modality sensed by the sensor;
    wherein said one or more sensors comprise a first sensor to detect acceleration and a second sensor configured to detect sound, said first sensor and said second sensor are configured to acquire data synchronously, said first sensor provides an indication of signal quality of the second sensor;
    a signal converter configured to receive the electrical signals from the one or more sensors and to convert the electrical signals to one or a plurality of sensor data signals, wherein the one or the plurality of sensor data signals comprises a data representation of at least one of the electrical signals that, when analyzed by a processor, determines stenosis of the vessel; and
    a power source and a shelf sensor, wherein the shelf sensor is configured to place the wearable device into a shelf mode in which power is either disconnected from the sensor assembly or the sensor assembly is placed into a low power mode.

2. The wearable device of claim 1, wherein the second sensor is a photo-plethysmogram (PPG) sensor that comprises at least one light source to direct light towards the vessel and at least one light detector to detect reflected light from fluid flowing through the vessel to obtain a volumetric measurement of the vessel.

3. The wearable device of claim 2, wherein the second sensor is an electrocardiography sensor.

4. The wearable device of claim 2, wherein the sensor assembly comprises an ultrasonic transducer and an ultrasonic sensor.

5. The wearable device of claim 2, wherein the one or more sensors of the sensor assembly comprises an acoustic sensor having a substantially flat sensitivity less than ten kilohertz.

6. The wearable device of claim 2, wherein the one or more sensors of the sensor assembly comprises a strain gauge having a sensitivity to a mechanical strain between about 0.1 hertz (Hz), and about 9 megahertz (Mhz).

7. The wearable device of claim 2, wherein the one or more sensors of the sensor assembly comprises a temperature sensor having a resolution below about 0.1 degrees C.

8. The wearable device of claim 2, wherein the one or more sensors of the sensor assembly comprises a temperature sensor, and wherein the signal converter is configured to sample electrical signals representing a temperature reading from the temperature sensor at about 8 hertz (Hz).

9. The wearable device of claim 2, wherein the one or more sensors of the sensor assembly comprises two or more temperature sensors configured to provide a differential temperature measurement.

10. The wearable device of claim 9, wherein a first temperature sensor is positioned within the patch to obtain a temperature reading of a first location distal to the AV access being an arteriovenous (AV) fistula and a second temperature sensor is positioned within the adhesive patch to obtain a temperature reading of a second location adjacent and distal to the AV fistula, wherein an inference of blood flow through the AV fistula is determine based on a difference between the first temperature and the second temperature.

11. The wearable device of claim 2, wherein the AV access corresponds to an arteriovenous (AV) fistula.

12. The wearable device of claim 1, wherein the one or more sensors of the sensor assembly comprises an acoustic sensor and an accelerometer.

13. The wearable device of claim 12, wherein the acoustic sensor is a piezoelectric device.

14. The wearable device of claim 13, wherein the piezoelectric device is made of one or more materials selected from the group consisting of polyvinylidene fluoride (PVDF), lead zirconate (PZT), and a composite including either PVDF or PZT materials.

15. The wearable device of claim 12, wherein the acoustic sensor is a microphone.

16. The wearable device of claim 15, wherein the microphone is implemented using a microelectromechanical system.

17. The wearable device of claim 15, wherein the vessel is the AV access corresponding to an arteriovenous (AV) fistula, and wherein the microphone is configured to measure an acoustic signature of blood flow through the AV fistula.

18. The wearable device of claim 17, wherein the adhesive patch is attached to a skin of the patient body in proximity to the AV fistula through a biocompatible adhesive having acoustic impedance.

19. The wearable device of claim 1 further comprising:
    a communications interface configured to communicate the one or the plurality of sensor data signals to a sensor data processing system.

20. The wearable device of claim 19, wherein the communications interface comprises a wireless transmitter configured to transmit the one or a plurality of sensor data signals to the sensor data processing system and the wireless transmitter is configured to communicate radio frequency signals.

21. The wearable device of claim 20, wherein the radio frequency signals are configured to be communicated using a near field communication protocol.

22. The wearable device of claim 19, wherein the communications interface comprises a wireless transmitter configured to transmit the one or a plurality of sensor data signals to the sensor data processing system and the wireless transmitter is configured to communicate using a cellular communications system.

23. The wearable device of claim 19, wherein the communications interface comprises a wireless transmitter configured to communicate using a wireless local area network system or a near field magnetic communication system.

24. The wearable device of claim 1,
wherein the shelf mode is configured to be automatically entered based at least in a part on readings from any one or more of:
magnetic sensors or switches;
optical sensors;
motion, acceleration or tilt sensors;
temperature sensors;
capacitive proximity sensors; and
mechanical switches.

25. The wearable device of claim 1, further comprising:
wherein the shelf mode is configured to be invoked by a microcontroller device and is configured to be exited based at least in part on readings from any one or more of:
magnetic sensors or switches;
optical sensors;
motion, acceleration, or tilt sensors;
temperature sensors;
capacitive proximity sensors; and
mechanical switches.

26. The wearable device of claim 24 or 25, wherein the readings are based at least in part on an interaction with a product packaging or an adhesive backing liner, and wherein the shelf mode is configured to be exited when the adhesive patch is removed from the product packaging.

27. The wearable device of claim 1, wherein the adhesive patch is configured to monitor an arteriovenous (AV) fistula being the vessel.

28. The wearable device of claim 27, wherein each sensor of the one or more sensors of the sensor assembly is configured to monitor a condition or state of the AV fistula.

29. The wearable device of claim 1, wherein the one or more sensors of the sensor assembly include a photo-plethysmogram (PPG) sensor that includes one or more light sources to detect reflected light from fluid flowing through the vessel.

30. The wearable device of claim 1, further comprising a third sensor configured to at least detect optical energy.

31. The wearable device of claim 30, further comprising a fourth sensor configured to measure electrocardiography signals.

32. A wearable device for sensing information relating to subcutaneous processes in a patient, the wearable device comprising:
an adhesive patch configured to attach to a body part of the patient at a location that provides subcutaneous access to an arteriovenous (AV) access;
a sensor assembly mounted on the adhesive patch, the sensor assembly comprises one or more sensors including a photo-plethysmogram (PPG) sensor that includes one or more light sources to detect reflected light from fluid flowing through the AV access to obtain a volumetric measurement of the vessel, the one or more sensors, including the PPG sensor, being configured to generate one or more electrical signals corresponding to a sensory modality sensed by the one or more sensors;
said one or more sensors further comprise a first sensor to detect acceleration and a second sensor configured to detect sound, said first sensor and said second sensor are configured to acquire data synchronously, said first sensor provides an indication of signal quality of the second sensor;
a signal converter configured to receive the electrical signals from the one or more sensors and to convert the electrical signals to one or a plurality of sensor data signals, wherein the one or the plurality of sensor data signals comprises a data representation of at least one of the electrical signals that, when analyzed by a processor, determines a thrombosis development or clinically actionable levels of stenosis; and
a power source and a shelf sensor, wherein the shelf sensor is configured to place the wearable device into a shelf mode in which power is either disconnected from the sensor assembly or the sensor assembly is placed into a low power mode.

33. The wearable device of claim 32, wherein the AV access corresponds to an arteriovenous (AV) fistula.

* * * * *